US006962569B2

(12) United States Patent
Smyser et al.

(10) Patent No.: US 6,962,569 B2
(45) Date of Patent: Nov. 8, 2005

(54) ISOMETRIC SYSTEM, METHOD AND APPARATUS

(75) Inventors: Michael A. Smyser, Galena, OH (US); Ronald L. Wiley, Oxford, OH (US); Thomas L. Harris, Powell, OH (US)

(73) Assignee: MD Systems, Inc., Westerville, OH (US)

( * ) Notice: Subject to any disclaimer, the term of this patent is extended or adjusted under 35 U.S.C. 154(b) by 82 days.

(21) Appl. No.: 10/268,363

(22) Filed: Oct. 10, 2002

(65) Prior Publication Data

US 2003/0093012 A1 May 15, 2003

Related U.S. Application Data

(60) Provisional application No. 60/330,265, filed on Oct. 18, 2001.

(51) Int. Cl.[7] .......................... A61B 5/103; A61B 5/117
(52) U.S. Cl. ..................................................... 600/595
(58) Field of Search ........................... 600/595; 601/23; 482/91, 1, 5, 111, 49, 8, 9, 901, 902; 73/379.02, 379.09

(56) References Cited

U.S. PATENT DOCUMENTS

| | | | |
|---|---|---|---|
| 4,884,445 A | * 12/1989 | Sadoff et al. | ............ 73/379.02 |
| 4,949,729 A | 8/1990 | Haski | |
| 5,398,696 A | 3/1995 | Wiley | |
| 5,904,639 A | 5/1999 | Smyser et al. | |

FOREIGN PATENT DOCUMENTS

WO 87/02567 5/1987

OTHER PUBLICATIONS

Advertisement for JAMAR® Hydraulic Hand Dynamometer.

Owners Manual, JAMAR® Hydraulic Hand Dynamometer; 1958.

Howden et al. "The Effects of Isometric Exercise Training On Resting Blood Pressure and Orthostatic Tolerance in Humans", *Experimental Physiology* 87.4, pp 507–515.

Vecht, R. J. Grahm GWS, Sever PS. "Plasma Noradrenaline Concentrations During Isometric Exercise." *Brit Heart J.* 1978;40:1216–20.

Chrysant SG. "Hemodynamic Effects of Isometric Exercise in Normotensive Hypertensive Subjects"; *Hypertension. Angiology* 1978:29(5):379–85.

Choquette, et al., "Blood Pressure Reduction in 'Borderline' Hypertensivies Following Physical Training" *Can. Med. Assoc. J.* 1108:699–703, 1973.

Clark, et al., "The Duration of Sustained Contractions of the Human Forearm of Different Muscle Temperatures", *J. Physiol.*, 143:454–473.

(Continued)

*Primary Examiner*—Max F. Hindenburg
*Assistant Examiner*—Brian Szmal
(74) *Attorney, Agent, or Firm*—Mueller and Smith, LPA

(57) ABSTRACT

System, method and apparatus for carrying out isometric exercises for either diagnostic purposes or therapeutic purposes. When employed in a diagnostic mode, the instrument is programmed to carry out standardized diagnostic regimens and during such regimens provides both visual and aural cues, carries out mathematical computations of force values and provides recordation of diagnostic data in archival memory. When employed in a therapeutic mode the apparatus may only be programmed within mandated therapeutic parameter limitations. During therapeutic trials, the user is visually and aurally cued throughout the test sequence and the therapeutic data evolved during the regimen is recorded and recoverable from archival memory.

108 Claims, 19 Drawing Sheets

OTHER PUBLICATIONS

Gilders, et al., "Endurance Training and Blood Pressure in Normotensive and Hypertensive Adults", *Med. Sci. Sports Exerc.* 21:629–636, 1989.

Harris, et al., "Physiological Response to Circuit Weight Training in Borderline Hypertensive Subjects", *Med. Sci. Sports Exerc.*, 19:246–252, 1987.

Hurley, et al., "Resistive Training Can Induce Coronary Risk Factors Without Altering $VO_{2\ max}$ or Percent Body Fat", *Med. Sci. Sports Exerc.* 20:150–154, 1988.

Kiveloff, et al., "Brief Maximal Isometric Exercise in Hypertension", *J. Am Geriatr. Socl*, 9:1006–1012, 1971.

Merideth, et al., "Exercise Training Lowers Resting Renal but not Cardiac Sympathetic Activity in Humans", *Hypertension*, 18:575–582, 1991.

Seals, et al., "The Effect of Exercise Training on Human Hypertension: A Review", *Med. Sci. Sports Exerc.*, 16:207–215, 1984.

Hanson P., et al., "Isometric Exercise: Cardiovascular Responses in Normal and Cardiac Populations", *Cardiology Clinics* 1987;5(2):157–70.

Wiley, et al., "Isometric Exercise Training Lowers Resting Blood Pressure", *Med. Sci. Sports Exerc.* 29:749–754, 1992.

Lind A R., "Cardiovascular Responses to Static Exercise" (*Isometrics, Anyone?*) Circulation 1970;41(2):173–176.

Mitchell, et al., Static (Isometric) Exercise and the Heart: Physiological and Clinical Considerations, *Ann Rev Med* 1974;25:369–81.

Mathiowetz, et al., "Grip and Pinch Strength: Norms for 6 to 19 Year Olds", *The American Journal of Occupational Therapy* 40:705–11, 1986.

Mathiowetz, et al., "Effect of Elbow Position on Grip and Key Pinch Strength", *The Journal of Hand Surgery* 10A:694–7, 1985.

Mathiowetz, et al., "Grip and Pinch Strength: Normative Data for Adults", *Arch Phys Med Rehabilitation* 66:69–72, 1985.

Mathiowetz, et al., "Reliability and Validity of Grip and Pinch Strength Evaluations", *The Journal of Hand Surgery* 9A:22–6, 1984.

* cited by examiner

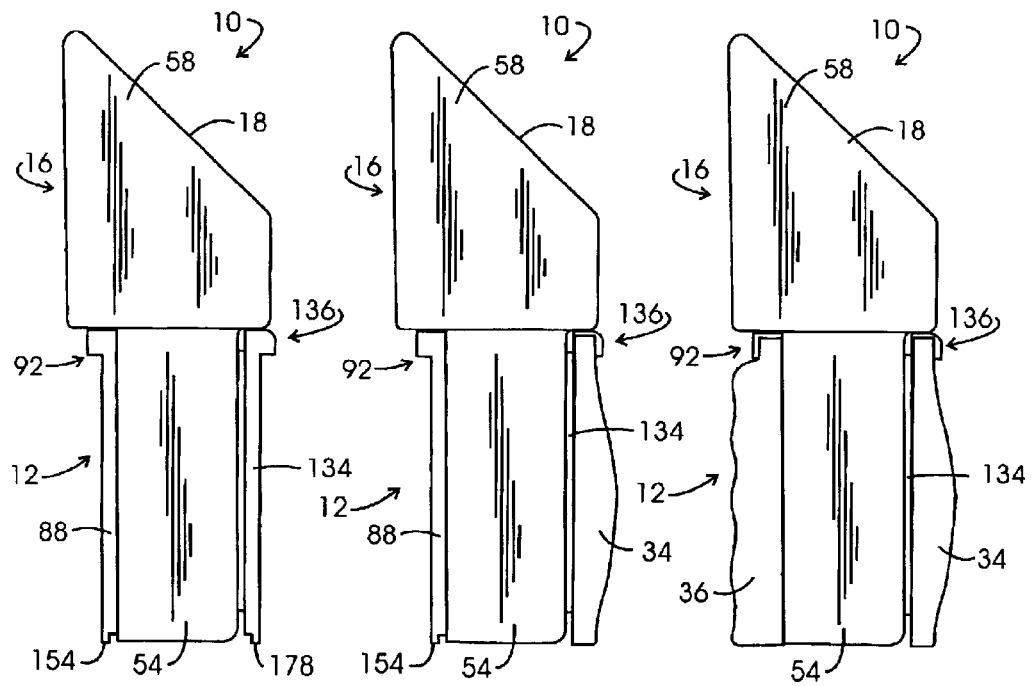
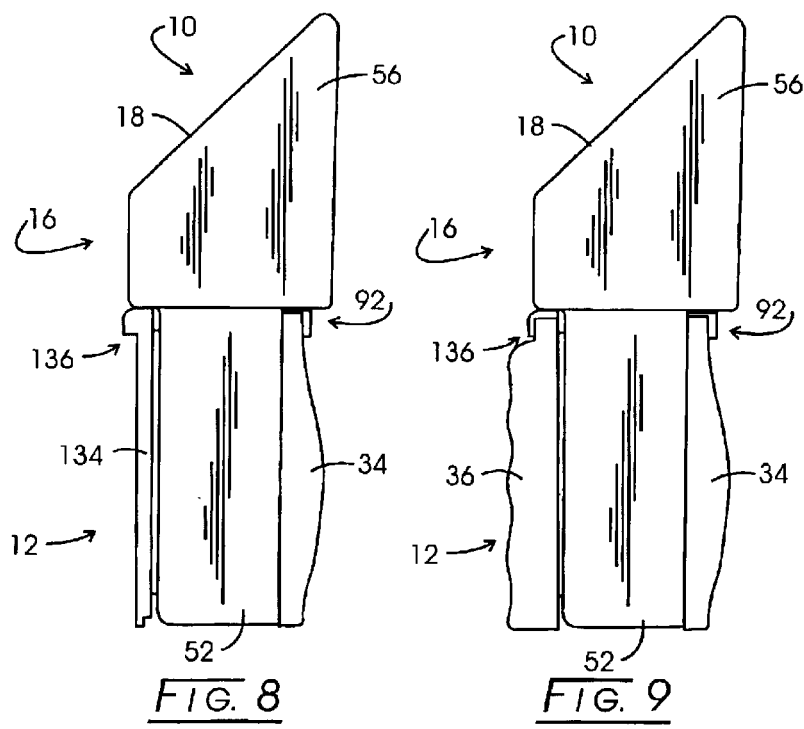

TO FIG. 12B

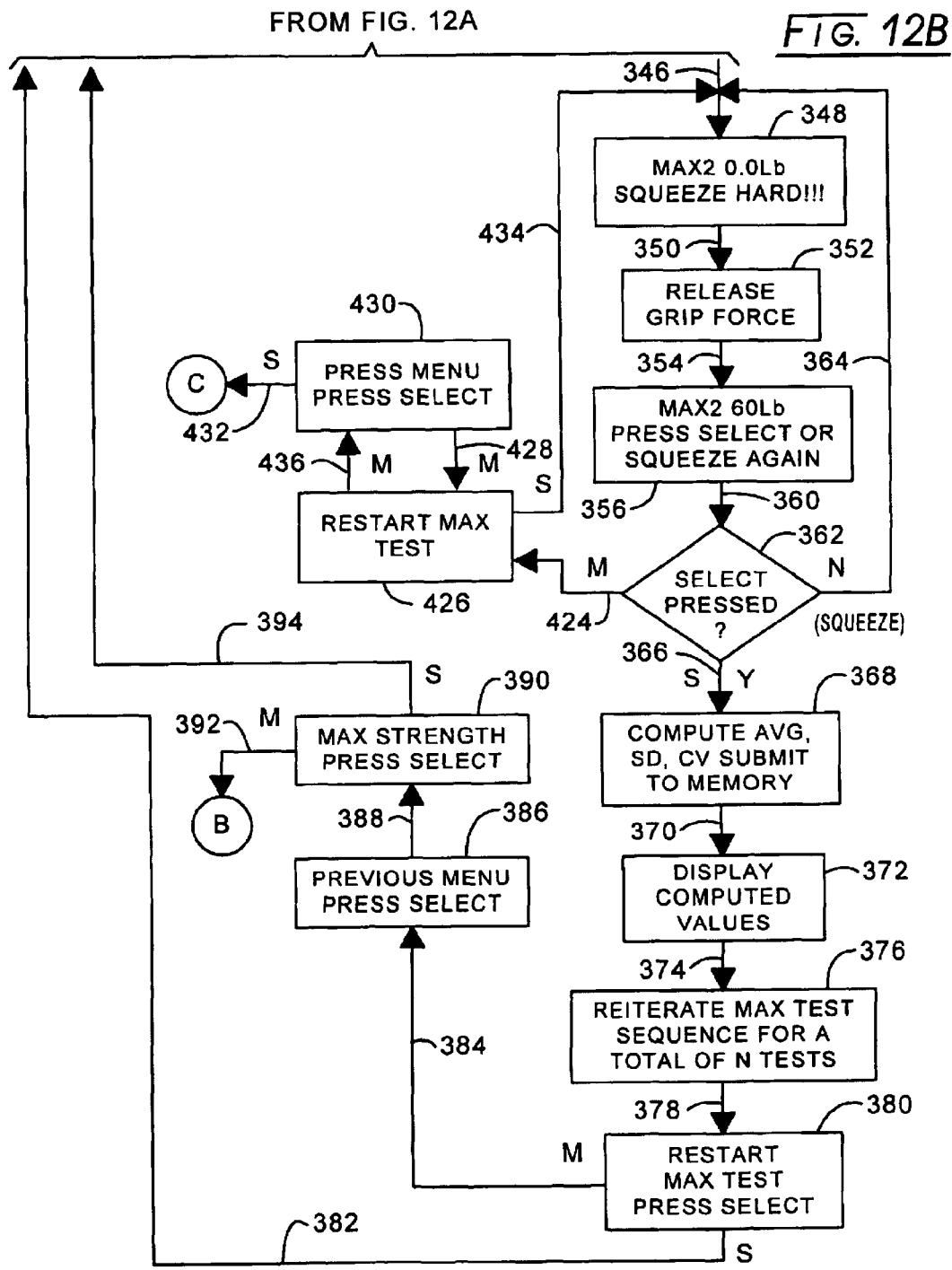

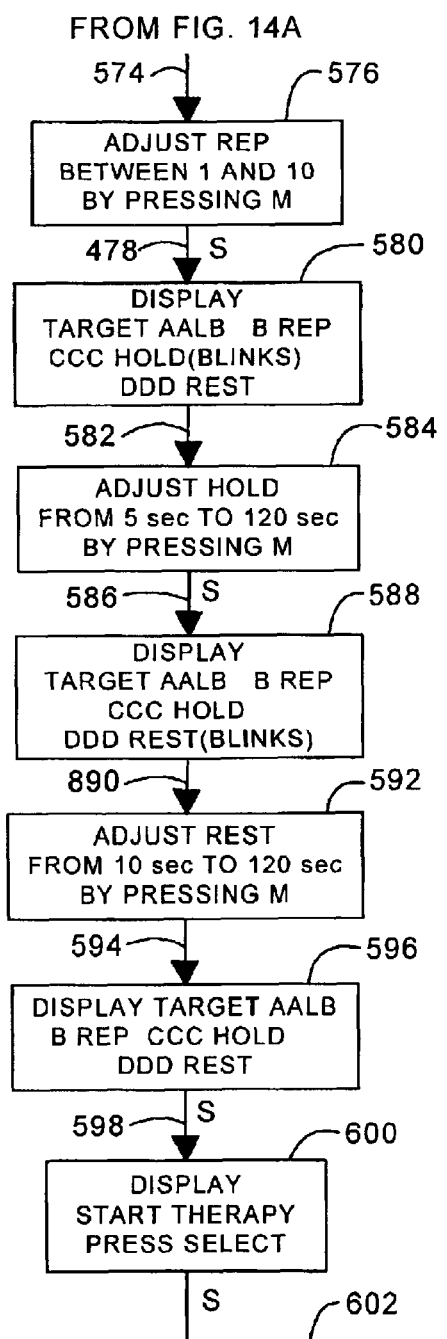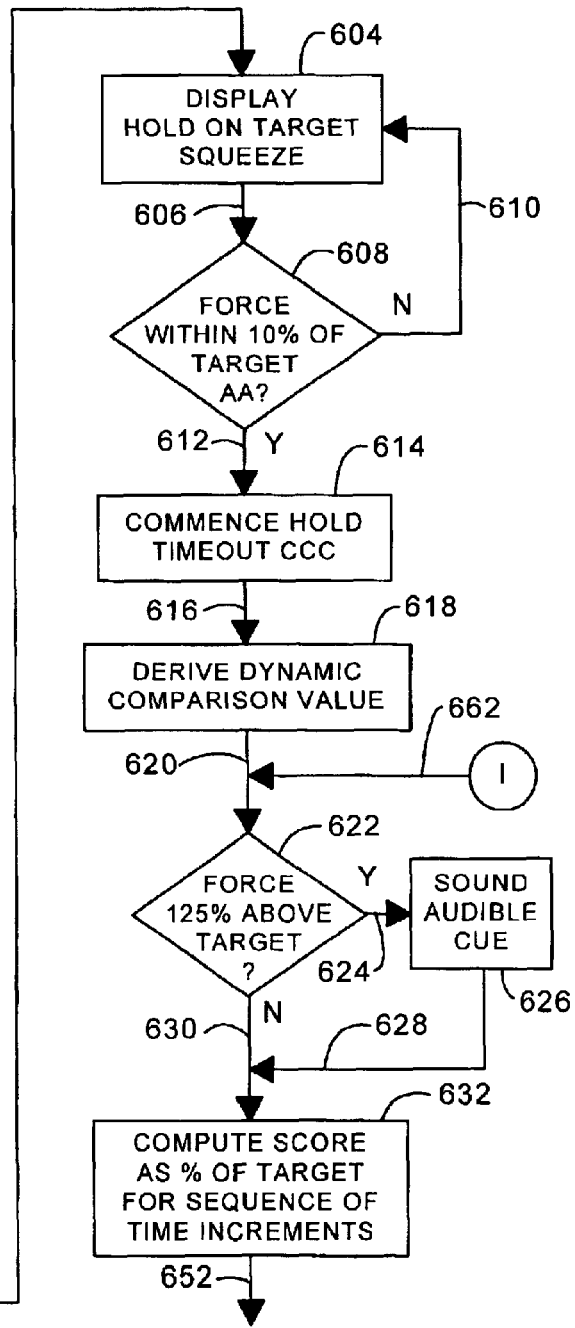
FIG. 14B

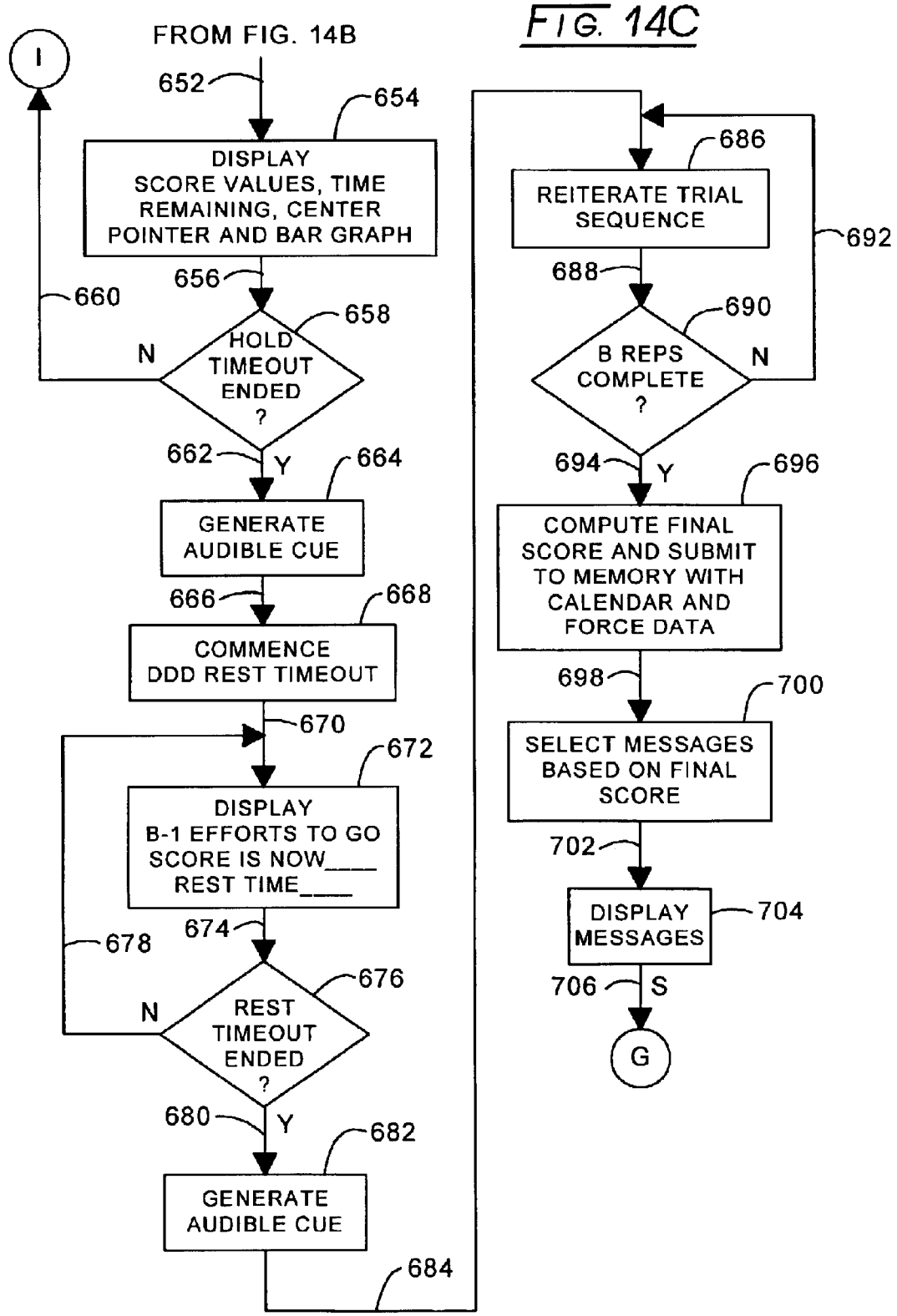

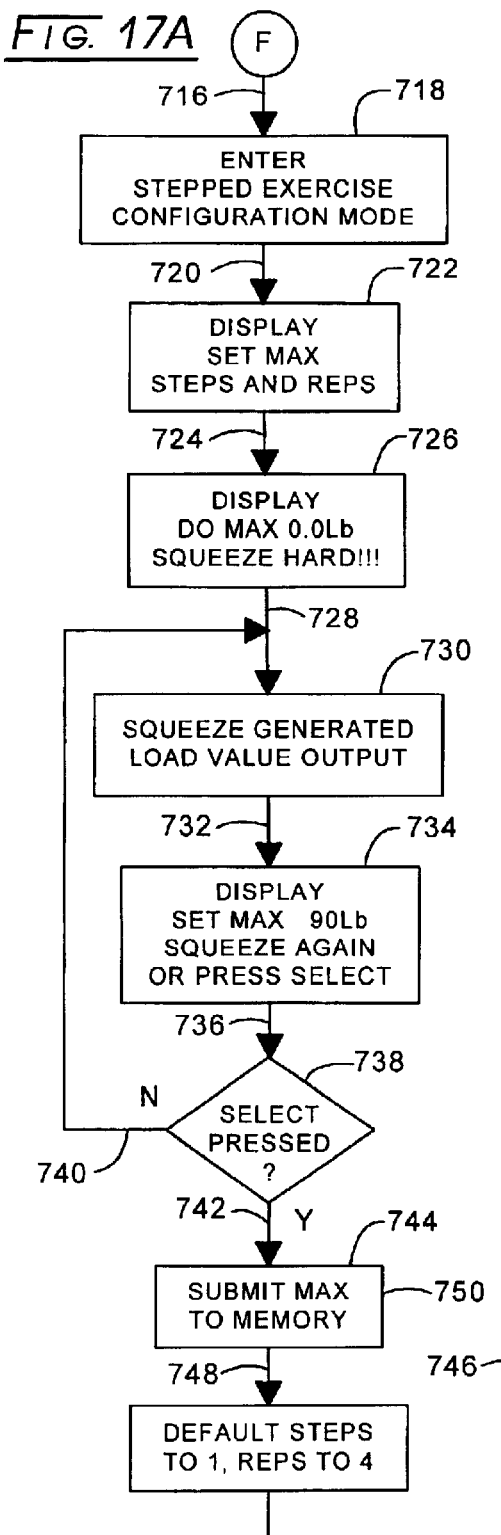
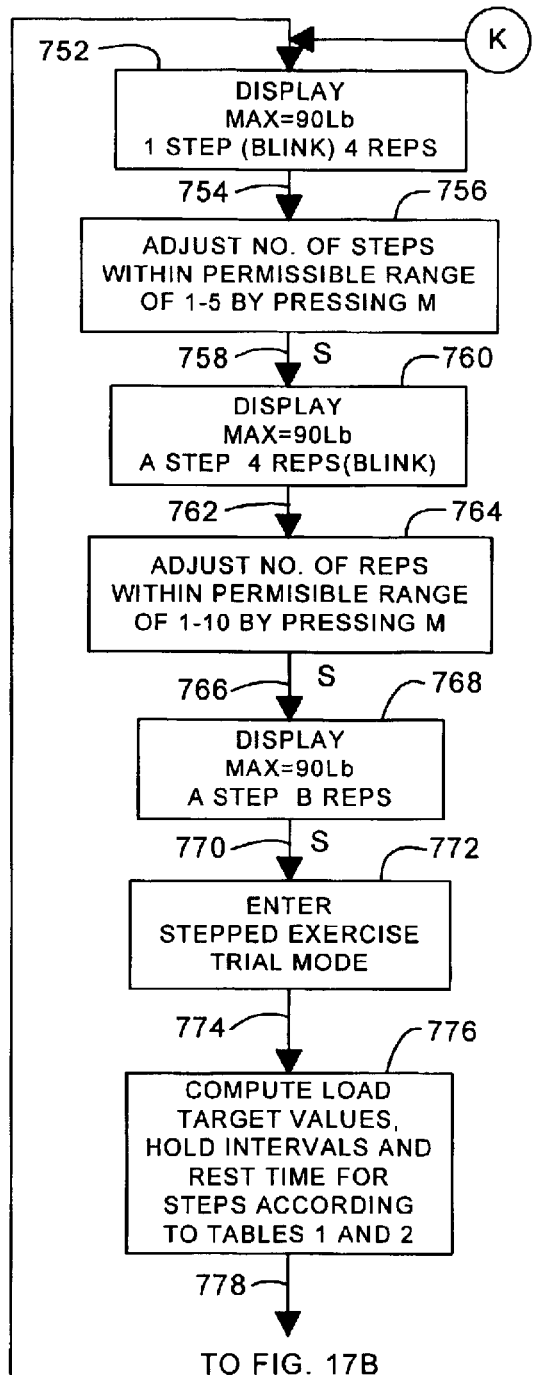
FIG. 17A

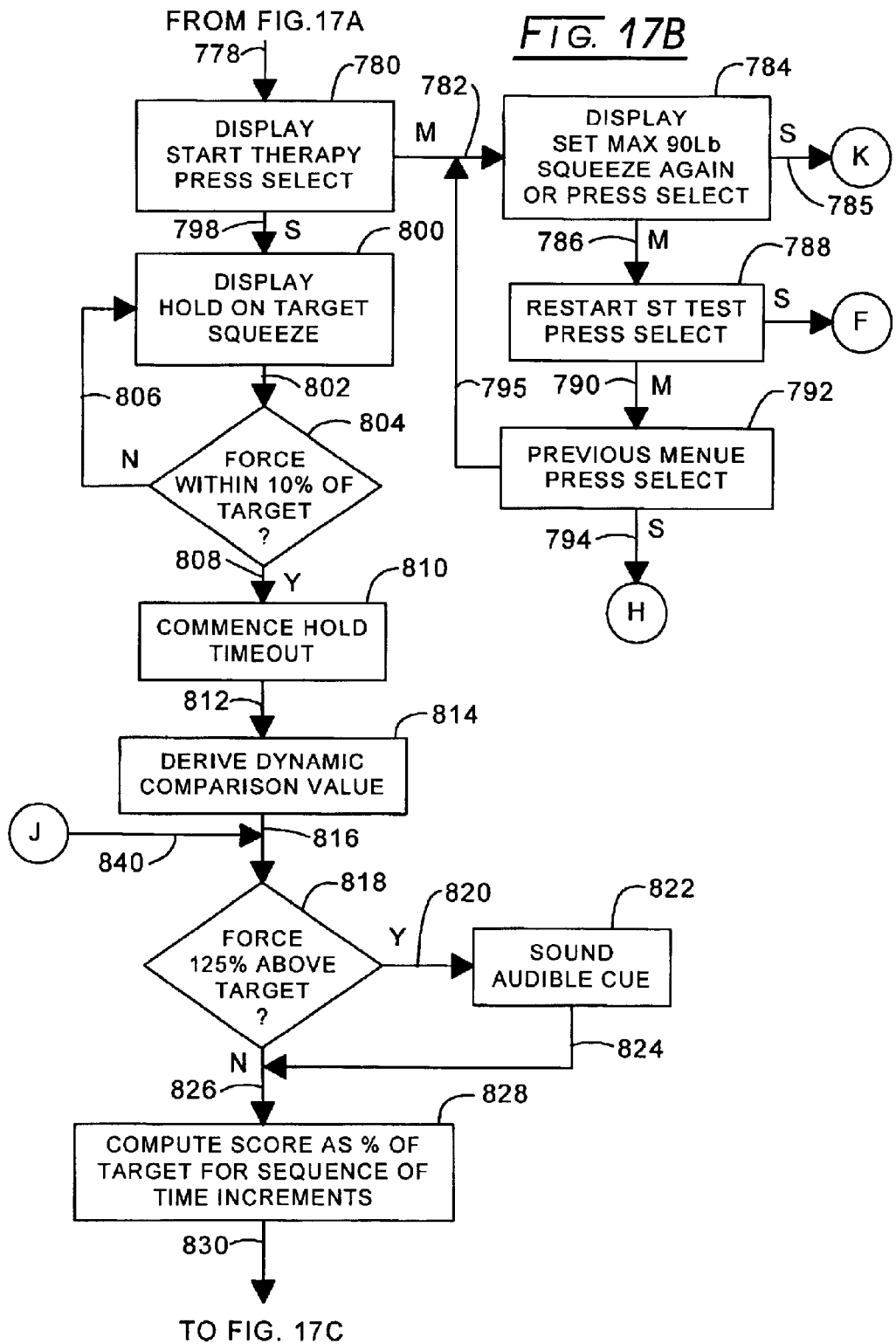

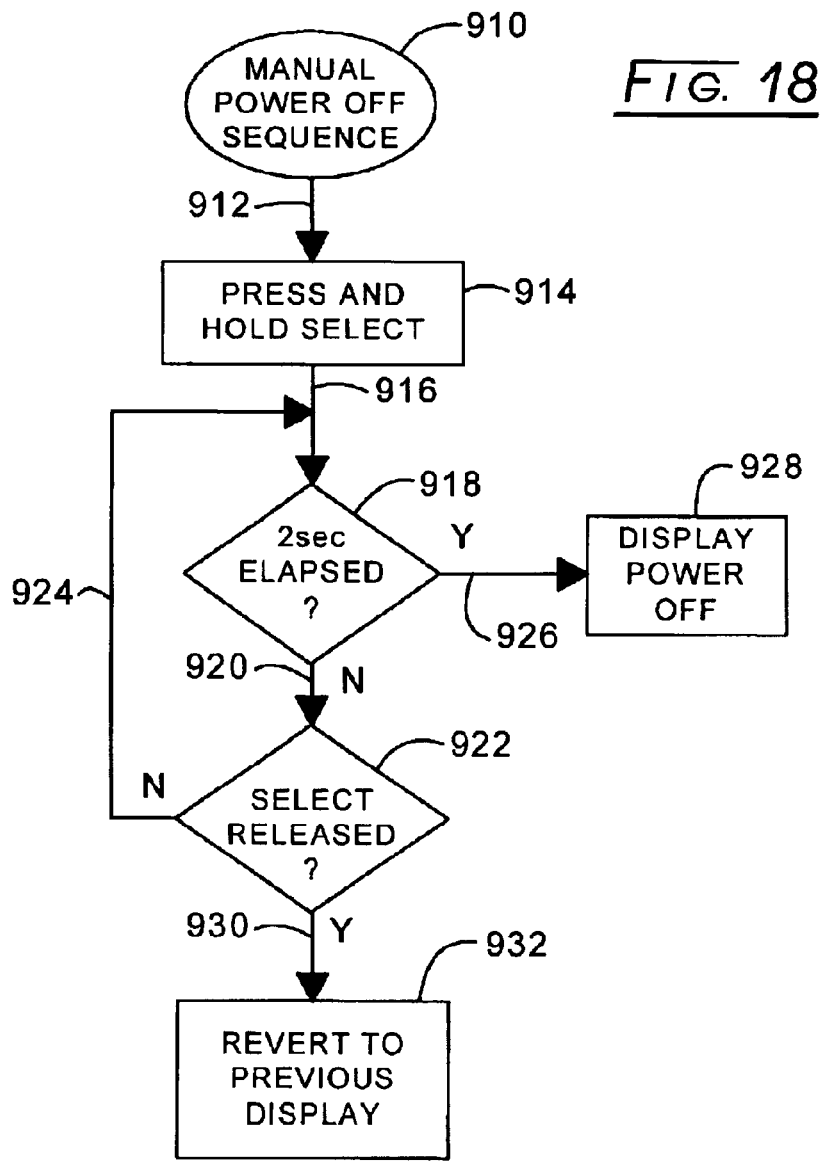

ISOMETRIC SYSTEM, METHOD AND APPARATUS

CROSS-REFERENCE TO RELATED APPLICATIONS

This application claims the benefit of Provisional Application No. 60/330,265, filed Oct. 18, 2001.

STATEMENT REGARDING FEDERALLY SPONSORED RESEARCH

Not applicable.

BACKGROUND OF THE INVENTION

The use of isometric as compared to rhythmic exercise in the general field of athletic strength development, as well as a therapy for strength recovery has been the subject of somewhat controversial discourse over the past decades. In general, such exercise has been considered to promote, for example, coronary risk factors. See generally:

(1) Vecht R J, Graham G W S, Sever P S. "Plasma Noradrenaline Concentrations During Isometric Exercise." *Brit Heart J.* 1978;40:1216–20.

(2) Chrysant S G. "Hemodynamic Effects of Isometric Exercise in Normotensive Hypertensive Subjects": *Hypertension. Angiology* 1978:29(5):379–85.

However, as such attitudes persisted, some investigators commenced to observe contradictions to these generally accepted beliefs. See for, example, the following publications:

(3) Buck, et al., "Isometric Occupational Exercise and the Incidence of Hypertension", *J. Occup. Med.*, 27:370–372, 1985

(4) Choquette, et al., "Blood Pressure Reduction in 'Borderline' Hypertensivies Following Physical Training" *Can. Med. Assoc. J.* 1108:699–703, 1973.

(5) Clark, et al., "The Duration of Sustained Contractions of the Human Forearm of Different Muscle Temperatures", *J. Physiol.*, 143:454–473, 1958.

(6) Gilders, et al., "Endurance Training and Blood Pressure in Normotensive and Hypertensive Adults", *Med. Sci. Sports Exerc.* 21:629–636, 1989.

(7) Hagberg, et al., "Effect of Weight Training on Blood Pressure and Hemodynamics in Hypertensive Adolescents", *J. Pediatr.* 1104:147–151, 1984.

(8) Harris, et al., "Physiological Response to Circuit Weight Training in Borderline Hypertensive Subjects", *Med. Sci. Sports Exerc.*, 19:246–252, 1987.

(9) Hurley, et al., "Resistive Training Can Induce Coronary Risk Factors Without Altering $VO_{2\,max}$ or Percent Body Fat" *Med. Sci. Sports Exerc.* 20:150–154, 1988.

(10) Hypertension Detection and Follow-Up Program Cooperative Group, "The Effect of Treatment on Mortality in 'Mild' Hypertension", *N. Engl. J. Med.*, 307:976–980, 1982.

(11) Kiveloff, et al., "Brief Maximal Isometric Exercise in Hypertension", *J. Am. Geriatr. Socl*, 9:1006–1012, 1971.

(12) Merideth et al., "Exercise Training Lowers Resting Renal but not Cardiac Sympathetic Activity in Humans", *Hypertension*, 18:575–582, 1991.

(13) Seals and Hagberg, "The Effect of Exercise Training on Human Hypertension: A Review", *Med. Sci. Sports Exerc.*, 16:207–215, 1984.

(14) Hanson P, Nagle F. "Isometric Exercise: Cardiovascular Responses in Normal and Cardiac Populations." *Cardiology Clinics* 1987;5(2): 157–70.

Such speculation on the part of these early observers was confirmed by Wiley in the 1990s, as described in U.S. Pat. No. 5,398,696 entitled "Isometric Exercise Method for Lowering Resting Blood Pressure and Grip Dynamometer Useful Therefore", issued Mar. 21, 1995 and as described in the following publication:

(15) Wiley, et al., "Isometric Exercise Training Lowers Resting Blood Pressure", *Med. Sci. Sports Exerc.* 29:749–754, 1992.

With the approach or protocol developed by Wiley, the isometric regimen is closely controlled both in terms of exerted force and in the timing of trials or exertions.

In contrast, earlier subjects or trainees undergoing isometric exercise stressed the involved musculature to their full or maximum capability (publication (11)) or at some submaximal force as long as it could be sustained, in either case only terminating with the onset of unendurable fatigue. Such approaches often have incurred somewhat deleterious results as evidenced by the injuries sustained in consequence of improper weightlifting procedures. Weightlifting procedures or endeavors exhibit a significant isometric factor. See generally:

(16) Lind A R. "Cardiovascular Responses to Static Exercise" (*Isometrics, Anyone?*) Circulation 1970;41 (2): 173–176.

(17) Mitchell J H, Wildenthal K. "Static (Isometric) Exercise and the Heart: Physiological and Clinical Considerations". *Ann Rev Med* 1974;25:369–81.

The diagnosis of patient hand-arm strength using isometric-based testing has been employed by physiologists, physical therapists and medical personnel for over three decades. These procedures function to evaluate hand-arm trauma or dysfunction and involve the patient use of a handgrip-based dynamometer. The dynamometer is grasped by the patient and squeezed to a maximum capability under the verbal instruction of an attending therapist or diagnostician. The hand dynamometer most widely used for these evaluations incorporates a grip serving to apply force through closed circuit hydraulics to a force readout provided by an analog meter facing outwardly so as to be practitioner readable. Adjustment of the size of the grip of the dynamometer is provided by inward or outward positioning of a forwardly disposed grip component. The dynamometers currently are marketed under the trade designation: "Jamar Hydraulic Hand Dynamometer" by Sammons Preston of Bolingbrook, Ill. An extended history of use of these dynamometers has resulted in what may be deemed a "standardization" of testing protocols. For instance, three of the above-noted grip length adjustments are employed in a standardized approach and verbal instructions on the part of the testing attendant, as well as the treatment of force data read from the analog meter are now matters of accepted protocol. In the latter regard, multiple maximum strength values are recorded, whereupon average strengths, standard deviations and coefficients of variation are computed by the practitioner. In one test, the instrument is alternately passed between the patient's right and left hands to derive a maximum strength output reading each 1.5 seconds or 2.5 seconds. Reading and hand recording strength values for such protocols has remained problematic. The protocols, for example, have been the subject of recommendations by the American Society of Hand Therapist (ASHT) and have been discussed in a variety of publications including the following:

(18) Mathiowetz V., Federman S., Wiemer D. "Grip and Pinch Strength: Norms for 6 to 19 Year Olds." *The American Journal of Occupational Therapy* 40:705–11, 1986.

(19) Mathiowetz V., Donohoe L., Renells C. "Effect of Elbow Position on Grip and Key Pinch Strength." *The Journal of Hand Surgery* 10A:694–7, 1985.

(20) Mathiowetz V., Dove M., Kashman N., Rogers S., Volland G., Weber K. "Grip and Pinch Strength: Normative Data for Adults." *Arch Phys Med Rehabilitation* 66:69–72, 1985.

(21) Mathiowetz V., Volland G., Kashman N., "Reliability and Validity of Grip and Pinch Strength Evaluations." *The Journal of Hand Surgery* 9A:22–6, 1984.

In about 1998, the above-noted Wiley protocols as described in connection with publication (12) above were incorporated in a compact, lightweight isometric device. Described in detail in U.S. Pat. No. 5,904,639 entitled "Apparatus, System, and Method for Carrying Out Protocol-Based Isometric Exercise Regimens" by Smyser, et al., the hand-held dynamometer has a hand grip which incorporates a load cell assembly. Extending from the hand grip is a liquid crystal display and two user actuated control switches or switch buttons. The display is mounted in sloping fashion with respect to the grip such that the user can observe important visual cues or prompts while carrying out a controlled exercise regimen specifically structured in terms of force values and timing in accordance with the Wiley protocols. This device is therapeutic as opposed to diagnostic in nature and is microprocessor driven with archival memory. External communication with the battery powered instrument is made available through a communications port such that the device may be configured by programming and, additional data, such as blood pressure values and the like may be inserted into its memory from an external device. Visual and audible cueing not only guides the user through a multi-step protocol but also aids the user in maintaining pre-computed target level grip compression levels.

Of course, it will be beneficial to incorporate improved diagnostic features for hand-arm evaluation techniques with therapist or practitioner designed therapeutic protocols specifically tailored to the condition of a given patient and which provide a control over such therapies clearly establishing such therapies as beneficial to strength development and recovery.

BRIEF SUMMARY OF THE INVENTION

The present invention is addressed to a system method and apparatus for carrying out a controlled isometric regimen by a user. Being microprocessor driven, the instrument is programmed to carry out established diagnostic as well as newly developed grip-based isometric regimens. When carrying out diagnostic procedures, the attending diagnostician may elect either a maximum grip test or a rapid exchange testing procedure. When employed for carrying out a diagnostic maximum grip test, the diagnostician selects configuration parameters and the instrument provides both visual and audible prompts and cues throughout the procedure. Maximum grip forces for each of the sequence of trials of this procedure are selected typically by the diagnostician and when so selected are recorded in instrument memory along with calendar data, and processor computed values for average grip force, standard deviation of the force values throughout a sequence of tests and corresponding coefficients of variation. At the termination of the diagnostic procedure, memory recorded test data are displayable to the diagnostician and may be downloaded through a communications port to a computer facility.

When utilized in a rapid exchange test mode, the attending diagnostician again programs the instrument with elected but standardized test parameters. At the commencement of and during the ensuing multi-trial test procedure, the patient may be provided with aural cues and, at the election of the diagnostician with visual cues. Grip force values for each trial are recorded in memory. As before, the instrument processor accesses that memory retained data and computes average grip force values, corresponding standard deviation for those force values and coefficient of variation, the values of which also are recorded in memory. At the termination of the multi-trial test regimen, the diagnostician is provided a successive display of the force values and associated computed information recorded in instrument memory.

For each of the diagnostic procedures, the widthwise extent of the instrument grip may be both varied in standard ½ inch increments from a minimum width. The grip is further configured such that the visually perceptible readout of the instrument may be viewed only by the diagnostician where deemed appropriate.

An important aspect of the therapeutic method associated with the instrument of the invention resides in the limiting of user performance to carry out the regimen of trials. In this regard, the instrument is programmed to perform only within predetermined and mandated test limits. Two therapeutic methods are described, a fixed therapy and a stepped therapy. Each therapeutic regimen is based upon an initial evaluation of the maximum gripping force capability of the user. Under that limitation, target load factors, hold on target load intervals, intervening rest intervals and trial repetition numbers may be elected only from pre-established and mandated memory retained ranges. The program also nominates rest intervals and hold on target intervals in correspondence with user elected target force factors. Thus, valuable strength recovery and development may be achieved but only within safe limits.

During each of the above therapeutic regimens, an audible warning is elicited whenever the user grip force value exceeds a computed upper limit. During each timed interval wherein the user is prompted to grip at a target force value computed with respect to the pre-tested maximum grip force, a dynamic bar graph and center point display is provided as a visual cue related to desired grip performance. Additionally, a rapid succession of score values are computed and the average thereof recorded at the end of each trial of a given regimen. These scores permit a therapist to access the quality of the performance of the user. In general, trial data is recorded in conjunction with calendar data and, as before, may be downloaded to a computer facility from an instrument contained communications port.

Other objects of the invention will, in part, be obvious and will, in part, appear hereinafter.

The invention, accordingly, comprises the method, system and apparatus possessing the construction, combination of elements, arrangement of parts and steps which are exemplified in the following detailed description.

For a fuller understanding of the nature and objects of the invention, reference should be made to the following detailed description taken in connection with the accompanying drawings.

BRIEF DESCRIPTION OF THE DRAWINGS

FIG. 5 is a side view of the apparatus of FIG. 1 showing a minimum grip width configuration;

FIG. 6 is a side view of the apparatus of FIG. 1 showing an orientation for user viewing of its display and a grip widthwise extent ½ inch greater than the grip orientation of FIG. 5;

FIG. 7 is a side view of the instrument of FIG. 1 showing an orientation for user viewing of its display and illustrating a grip widthwise extent of maximum value;

FIG. 8 is a side view of the instrument of FIG. 1 showing an orientation for diagnostic viewing and a grip widthwise extent corresponding with that of FIG. 6;

FIG. 9 is a side view of instrument of FIG. 1 showing a display orientation for viewing of a display by a diagnostician and having a grip widthwise extent corresponding with that of FIG. 7;

FIGS. 12A and 12B combine as labeled thereon to provide a flow chart of a maximum grip test diagnostic procedure;

FIGS. 14A–14C combine as labeled thereon to illustrate a flow chart describing a therapeutic fixed exercise regimen carried out by the instrument of FIG. 1;

FIGS. 17A–17C combine as labeled thereon to illustrate a flow chart of a step therapeutic exercise which may be carried out with the instrument of the invention;

FIG. 18 is a flow chart showing an intentional power off sequence; and

DETAILED DESCRIPTION OF THE INVENTION

Isometric exercise apparatus under which the methodology of the invention may be carried out is lightweight, portable, battery powered and sufficiently rugged to withstand the compressive pressures which it necessarily endures during use. The instrument is programmable such that it may be utilized by a therapeutic practitioner for diagnostic purposes employing established grip test modalities. Strength measurements carried out during these modes are compiled in memory and the practitioner is afforded calculated values for average grip force, standard deviation and coefficient of variation with respect to grip force trials. Furthermore, individual strength measurements compiled in these averages, whether taken rapidly or slowly, are stored in memory and may be reviewed by the therapist.

Additionally, the instrument is employable as a therapeutic device. First a protocol is nominated by prescribing nominal parameters of the effort. Each isometric regimen is controlled initially by requiring that a maximum grip strength be established for each individual patient or user. Then, the practitioner may elect parameters of grip force and timing under mandated memory contained parameter limits. Accordingly, the user will be unable to carry out strength enhancement therapies which would otherwise constitute an excessive grip force regimen. For carrying out the noted diagnostic procedures as well as therapy activities, the grip widthwise extent is variable from 1⅞ inches to 2⅞ inches, such variation being adjustable in ½ inch increments. This is in keeping with standardized diagnostic practices. Further with respect to diagnostic procedures, the display or readout of the instrument can be adjusted with respect to the grip structuring such that only the practitioner or therapist may observe the data which is being developed during a diagnostic protocol.

Figure 1:
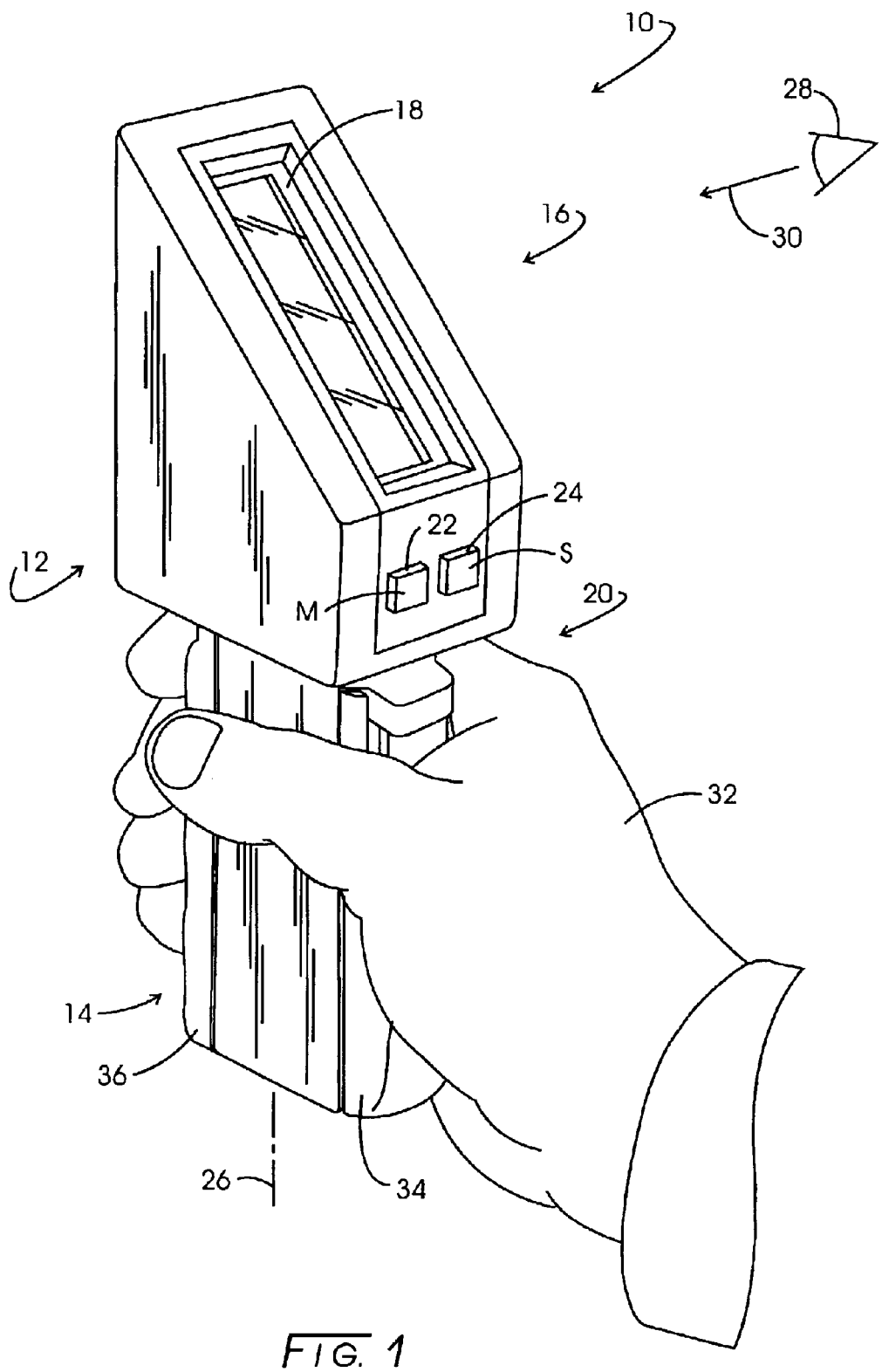
FIG. 1 is a perspective view of apparatus according to the invention showing its orientation with respect to a users hand wherein its display is viewable by such user.

Looking to FIG. 1, the instrument or apparatus is represented generally at 10 as having a housing identified generally at 12. Housing 12 is formed of acrylonitrile butadiene styrene (ABS) and, thus, is resistant to impact phenomena and the like. FIG. 1 shows that the housing 12 includes a hand grasping portion 14 and an integrally formed interacting portion 16. Interacting portion 16 supports a readout assembly 18 which is configured as an elongate liquid crystal display (LCD). Additionally located at the interacting portion are two finger actuable switches represented generally at 20. Of these switches, switch 22 is designated as a "menu" switch, while switch 24 is designated as a "select" switch. Note that the readout assembly 18 is angularly oriented with respect to the grip axis 26 of the apparatus 10. With this configuration, the user may observe prompts and cues appearing at the readout 18 as represented by the symbolic user eye station 28 and line of sight represented symbolically at arrow 30. In this regard, note that the hand 32 of the user is grasping the hand grasping portion 14. For the arrangement shown, the hand grasping portion 14 is represented as exhibiting its largest widthwise extent, i.e., 2⅞ inches. To gain this larger widthwise extent, auxiliary grip components 34 and 36 are employed in conjunction with the hand grasping portion 14. These auxiliary grip components will be seen to be removable as well as universally positionable so as to provide the noted widthwise adjustments in ½ inch increments.

Figure 2:
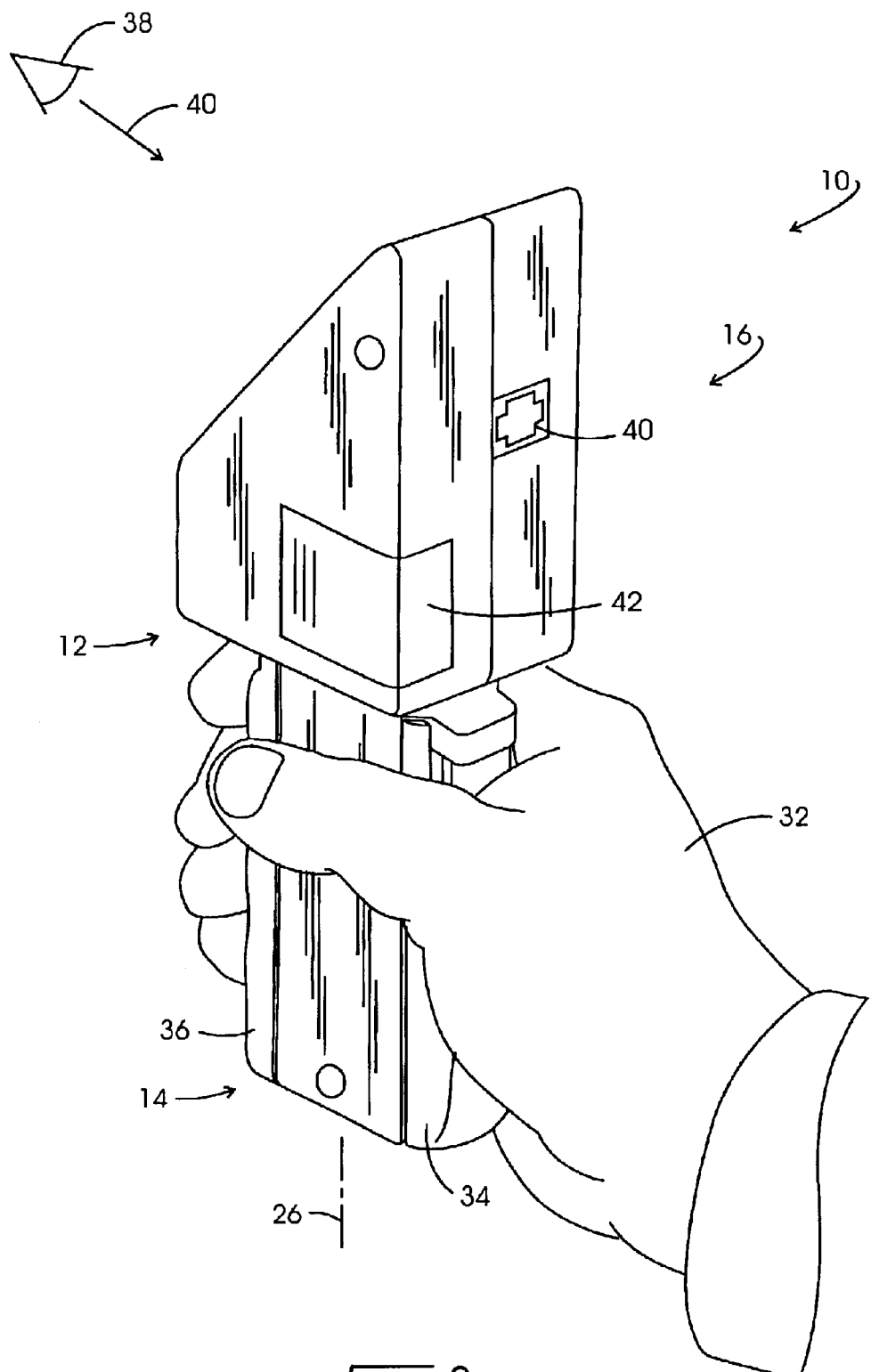
FIG. 2 is a perspective view of the apparatus of FIG. 1 showing the orientation of the apparatus with respect to the users hand wherein the display thereof is not visually accessible to the user.

Referring to FIG. 2, the instrument 10 is shown as it is employed for diagnostic activities. For this purpose, the auxiliary grip components 34 and 36 as seen in FIG. 1 have been reversed in their orientation at hand grasping portion 14. Note, additionally, that the symbolic eye station at 38 is now that of the diagnostician with a line of sight as represented symbolically at arrow 40 addressing the readout 18 (not shown). Note that the line of sight 40 is directed toward the auxiliary grip component 36 and the data readout for diagnostic purposes is not visually available to the user whose hand is represented at 32. Seen additionally in FIG. 2 is a serial communications port 40 and a battery compartment access cover 42. This serial port offers, for diagnostic purposes, the instantaneous transfer of real-time data to remote monitoring and data archiving equipment.

Figure 3:
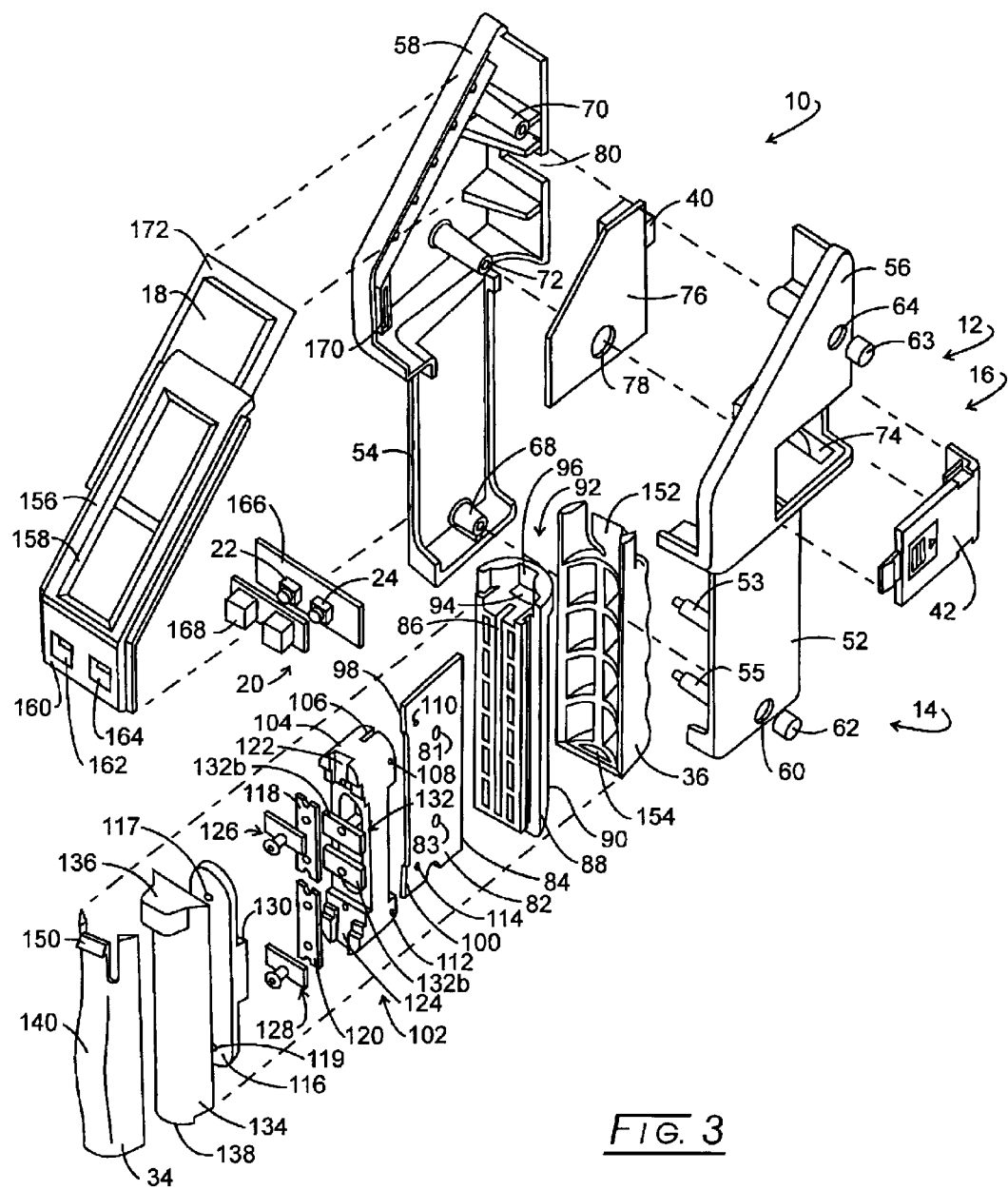
FIG. 3 is an exploded perspective view of the apparatus of FIG. 1.

Looking to FIG. 3, an exploded perspective view of the apparatus 10 is provided. In the figure, the grasping portion 14 is seen to be comprised of two mirror image sides 52 and 54. Integrally molded with the sides 52 and 54 are the two housing components of the interactive portion 16 as shown respectively at 56 and 58. Plastic inserts or plugs are shown at 60 and 62 which are insertable within respective screw cavities 64 and 66. Extending from grasping portion side 54 is an integrally molded screw receiving post 68. In similar fashion, screw receiving post 70 is integrally formed with and extends from component 58. Additionally, a screw receiving post 72 extends from component 58. Post 72 receives a screw inserted through a battery cavity 74 inwardly disposed from cover 42. Post 72 additionally functions to contribute to the support of a printed circuit board 76 by virtue of its insertion through an aperture 78 formed therein. Note that the printed circuit carrying board 76 also supports communications port 40. In this regard, the port 40 extends into a rectangular opening 80 formed within interactive portion 58 of housing 12. Further extending inwardly from component 52 are two force plate support plates 53 and 55

Disposed centrally within the cavity defined by gripping portion sides 52 and 54 is a steel thrust plate 82 having a thickness and rigidity elected to withstand compressive gripping forces which may range, for example, up to about 205 pounds. Plate 82 is configured with two holes 81 and 83 which are used to restrain the plate from disengaging from the assembly when fitted over respective posts 53 and 55. Elongate side 84 of thrust plate 82 is configured for insertion within an elongate groove 86 of a base grip component 88. Grip component 88 is formed of a rigid plastic and includes an outwardly disposed base grasping surface 90 upwardly located in adjacency with the grasping surface 90 is one component of a base connector assembly represented generally at 92 and which is seen to be integrally molded with the grip component 88 and incorporates a slot or opening 94 in conjunction with a tab receiving trough 96. A tab component (not shown) of the base connector assembly feature of the base grip component 88 will be seen to extend from the end thereof opposite connector assembly component 92.

Two oppositely disposed edge extensions 98 and 100 of the thrust plate 82 are configured for operative association with a load cell assembly represented generally at 102. Load cell assembly 102 includes an elongate steel base 104 incorporating two slots for receiving extensions 98 and 100, one such slot being revealed at 106. Connection between the base 104 and thrust plate 82 is provided by pins (not shown) which extend through mated bores 108 and 110 and 112 and 114. The load cell assembly 102 further includes an elongate outer force component 116. Two field plate-form load cells 118 and 120 are mounted from load cell mount structures shown, respectively at 122 and 124 formed within base 104. Such mounting is in cantilever fashion, the load cell 118 being attached to mount 122 by a screw and mounting plate assembly 126. Similarly, load cell 120 is attached in cantilever fashion to mount structure 124 by a screw and mounting plate assembly 128. Outer force component 116 is seen to have a centrally disposed rectangular post portion 130 which is attached by a connector plate assembly to the mutually inwardly extending ends of the load cells 118 and 120. The attachment plate assembly for this union is seen in general at 132. Assembly 132 is seen to be formed of two plate components 132a and 132b coupled, in turn, to load cells 120 and 118. Screws are use to effect the attachment.

The base grip component positioned oppositely of base grip component 88 is shown at 134. In similar fashion as component 88, the base grip component 134 is configured with a base connector assembly having one component at 136 which incorporates a slot and trough (not shown) in similar fashion as described at 92 in connection with component 88. a tab protrusion of generally cylindrical configuration shown at 138 is disposed oppositely from connector assembly component 136. The rigid plastic base component 134 is attached to elongate outer force component 116 of the load cell assembly 102. This attachment is provided by the insertion and crimping of two posts 134a and 134b (FIG. 4) within respective holes 117 and 119 formed within force component 116. a slot in component 134 is provided to positively locate it onto the outer profile of component 116. In general, posts 134a and 134b (FIG. 4) are inserted through holes 117 and 119 and then melted with a hot iron to mechanically secure the two pieces 134 and 116 together as one sub-assembly. With the arrangement shown, gripping compressive force is asserted from the base component 188 through the thrust plate 82 into the load cell assembly 102. This force is counteracted by gripping force asserted from base gripping component 134.

Auxiliary grip component 34 is shown in the figure in spaced adjacency with respect to the base grip component 134. Auxiliary component 34 is configured with an outwardly disposed auxiliary grasping surface of generally half cylindrical cross section with a grasping surface profile curved concavely outwardly, for example, at region 140. This curvature is provided for enhancing grip contact with the palm of the user hand and for applying force centrally to the load cell assembly. Component 34 is formed with an auxiliary connector assembly which includes a flexible engaging tab 150 configured for insertion within the connector component 136 of base grip component 134. Connection at the opposite end is provided by a curved slot (not shown) which receives the tab protrusion 138 of base grip component 134. The connector assemblies are universal such that each of the auxiliary grip components may be mounted upon either of the base grip components 88 or 134. In this regard, not that a similar flexible engaging tab 152 is positioned upwardly upon auxiliary grip component 36. Similarly, the component 36 is configured having a curved slot 154 at its opposite end which receives tabs, for example, as at 138. The mounting of either auxiliary grip component 36 or 34 will increase the widthwise extent of the grip by one half inch. Accordingly, with both auxiliary grip components installed, the widthwise extent of the grip is increased to 2⅞ inches.

Interacting region 16 also includes a top cover 156. Formed, as the other components, of ABS plastic, the cover 156 includes a rectangular bezel opening 158 within which the LCD 18 is positioned. Integrally formed with top cover 156 is a downwardly depending switch cover 160 through which two rectangular openings 162 and 164 are provided. The switching function 20 is mounted upon a separate circuit board 166 which is seen to carry two push actuated switches as earlier described at 22 and 24 and identified by the same numeration in the instant figure. Located over the switches 22 and 24 is a flexible polymeric cover 168 formed of a flexible polymeric material such as Santoprene, a thermoplastic elastomer marketed by General Polymers of Charlotte, N.C. Circuit board 166 is supported between two slots formed in the interior of side components 56 and 58, one of these slots is seen at 170. The LCD 18 is mounted upon a circuit board 172 supported in turn, from interactive components 56 and 58. A bus-type wiring harness electrically associates the switching function 20, LCD 18, load cell assembly 102, the battery within compartment 74 and the circuitry carried by circuit board 76.

Figure 4:
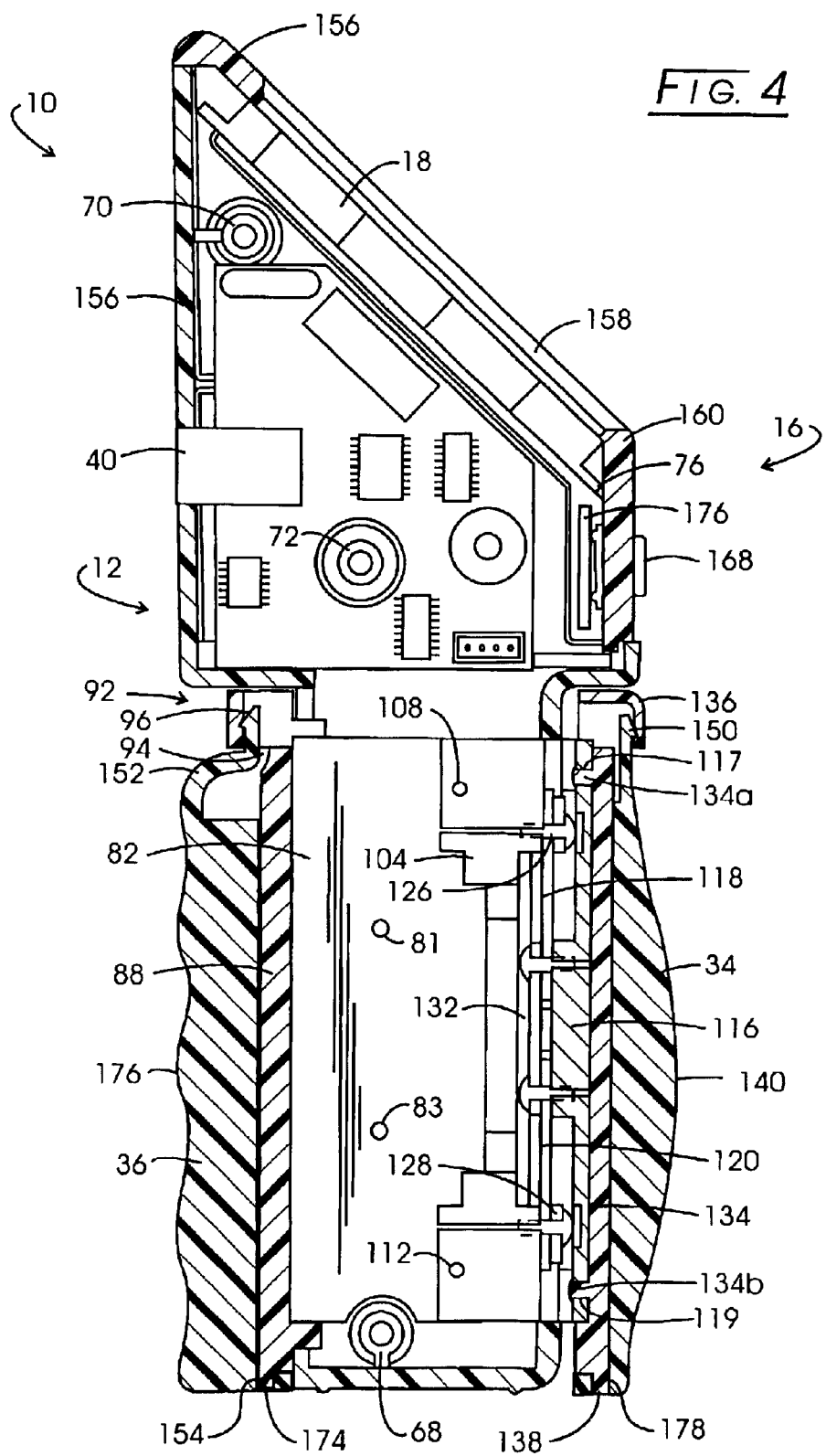
FIG. 4 is a side sectional view of the apparatus of FIG. 1.

A sectional view of the instrument 10 is provided at FIG. 4. In the figure, base grip component 88 is shown in conjunction with base connector assembly component 92. In that regard, the slot 94 again is revealed as well as the tab receiving trough 96. At the opposite end, the base connector assembly includes an outwardly extending arcuate tab 174. Auxiliary gripping component 36 is shown coupled to the base grip 88. Note that the auxiliary component 36 has a grasping surface 176, the profile of which is undulatory to provide a finger grasping configuration. This undulatory profile further functions to provide a finger grasping configuration which centers the gripping force on handle 88. The lower portion of the base grip component 88 is seen to be formed having an outwardly extending arcuate tab 174 which slideably nests within the corresponding arcuate slot 154 in auxiliary grip 36. The connector assembly for base grip component 134 is identical. In this regard, the component 134 includes an arcuate outwardly extending tab 138 and a slotted receiver 136 structured identically as that described at 92. Auxiliary grip component 34 is connected to base grip component 134 by sliding a protruding tab or tongue 138 into arcuate slot 178. Additionally, the flexible engaging tab 150 is shown extending through a slot in connector component 136.

FIGS. 5–7 illustrate variations of grip widthwise extent available for utilization of instrument 10 in conjunction with therapeutic protocols. In general, for such therapeutic protocols, the readout assembly 18 is arranged to face the eye station of the user. In FIG. 5, no auxiliary grip components are mounted upon either base grip component 88 or base grip component 134. Accordingly, the widthwise extent of the grip is 1⅞ inch. Looking to FIG. 6, the palm engaging auxiliary grip component 34 is shown mounted over base grip component 134. This increases the widthwise extent of the grip for therapeutic applications to 2⅜ inches. FIG. 7 illustrates the utilization of both auxiliary grip components 34 and 36 to provide a grip widthwise extent of 2⅞ inches. As before, the auxiliary grip components are arranged such that the user may observe readout 18.

FIGS. 8 and 9 illustrate grip arrangements particularly suited for diagnostic purposes wherein the diagnostician has exclusive access visual to the readout assembly 18. In FIG. 8, base grip component 134 is combined with auxiliary grip component 34 to provide a widthwise grip extent of 2⅜ inches. Removal of the auxiliary grip component 34 returns the grip widthwise extent to 1⅞ inches.

In FIG. 9, both auxiliary grip components 34 and 36 are employed to provide a maximum widthwise grip extent of 2⅞ inches. It may be observed in FIGS. 8 and 9 that the positioning of the auxiliary grips is reversed in the sense of the grip configuration shown in FIGS. 5–7.

Figure 10:
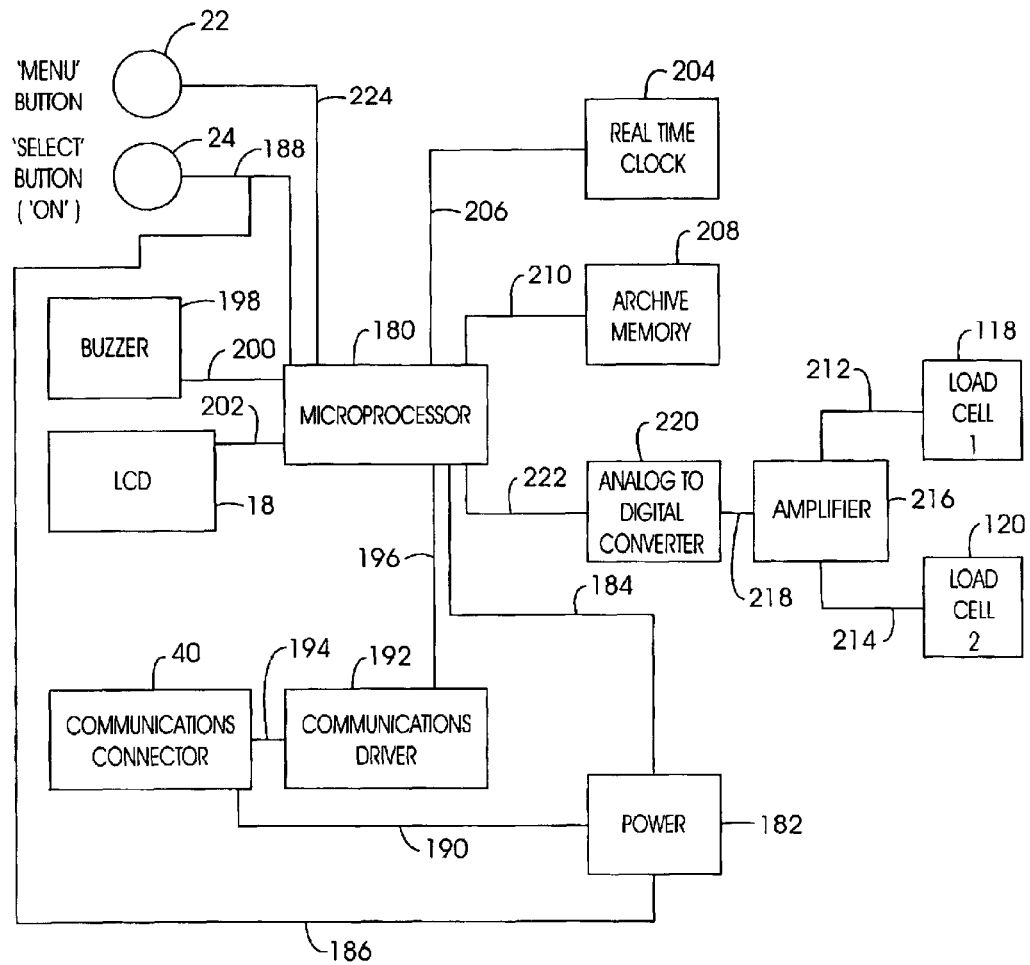
FIG. 10 is a block diagrammatic drawing of the circuit employed with the apparatus of FIG. 1.

Turning to FIG. 10, a block diagrammatic representation of the controller components of instrument 10 is revealed. In general, the instrument 10 is microprocessor driven, for example, employing a type 8051 microprocessor as represented at block 180. The controller is powered by a standard 9 volt battery. That voltage then is regulated to 5 volts for use by the circuit components. A power supply to the strain gauge implemented load cells 118 and 120 is dropped by a resistor such that the maximum current applied is limited to 50 milliamps. Such power supply is represented in the figure at block 182 which, in turn, is seen to be associated with microprocessor 180 via line 184 and with switch 24 via lines 186 and 188. Note that switches 22 and 24 respectively are labeled "menu" and "select". Switch 24 serves the additional function of an on switch or enablement switch. Power also is seen to be supplied to the communications connector 40 as represented at line 190. Communications connector 40, in turn, is seen coupled to a communications driver 192 as represented at line 194. Driver 192 associated with the microprocessor 180 as represented at line 196. The microprocessor 180 also provides control over an annunciator or buzzer as represented at block 198 and line 200. Similarly, control to the liquid crystal display (LCD) 18 from microprocessor 180 is represented at line 202. A real-time clock is provided with the controller circuit as represented at block 204. Time and date data from that clock are used in conjunction with the monitoring and memory features of the instrument 10 such that important data, including date and time of a given trial regimen can be retained in memory and downloaded via the communications port 40 when called for. The association of the real-time clock function 204 and microprocessor 180 is represented at line 206. Archival memory as well as temporary memory are provided with the controller. Archival memory may be provided, for example, as an electrically erasable programmable read only memory (EE PROM), an 8 kilobyte device which requires no power to sustain its memory retention, i.e., it is non-volatile. The archival memory is represented at block 208 and its association with the microprocessor 180 is represented at line 210.

Load cells 118 and 120 are represented with that numeration in FIG. 10. These load cells are each configured as a four resistance balance bridge-type load cell. The outputs of load cells 118 and 120 are directed to an amplification function as represented by respective lines 212 and 214 extending to amplifier block 216. The output of amplifier 216 is represented at line 218 extending to an analog-to-digital converter function represented at block 220. Correspondingly, output of the converter function 220 is directed to the microprocessor 180 as represented at line 222. Microprocessor 180 converts the signal to a force value in pounds or kilograms which is displayed in the LCD 18. The menu switch 22 is shown associated with microprocessor 180 via line 224, while the select switch 24 is associated with that processing function as represented at line 188.

Each of the instruments 10 is calibrated using nineteen combinations of six standard weights. A best fit is determined and the instrument is called upon to have a root mean square error (RMS) of 0.1 pounds or less to pass calibration requirements. Once the calibration constants have been determined, the system is loaded with two redundant copies of the calibration constants. The zero point of the load cell is monitored at all times during the use of the instrument 10. If a drift is found, then a warning is shown at the LCD display 18. If any lead wire to the load cell becomes disconnected, then the built-in monitoring detects this occurrence, shows an error message, and disables further use of instrument 10 until the power is reset. These features insure that the force reading shown is accurate and true. Absolute values of the outputs of load cells 118 and 120 are summed to provide a force output signal. In general, the load measurement accuracy of instrument 10 is better than 0.1 pound of 0.1% of applied force whichever is greater.

In the discourse to follow, the sequences of the program protocol carried out by instrument 10 are represented in flow chart fashion. In general, these flow charts commence with a configuration sequence if desired and then look to two diagnostic protocols followed by two therapeutic protocols.

Figure 11:
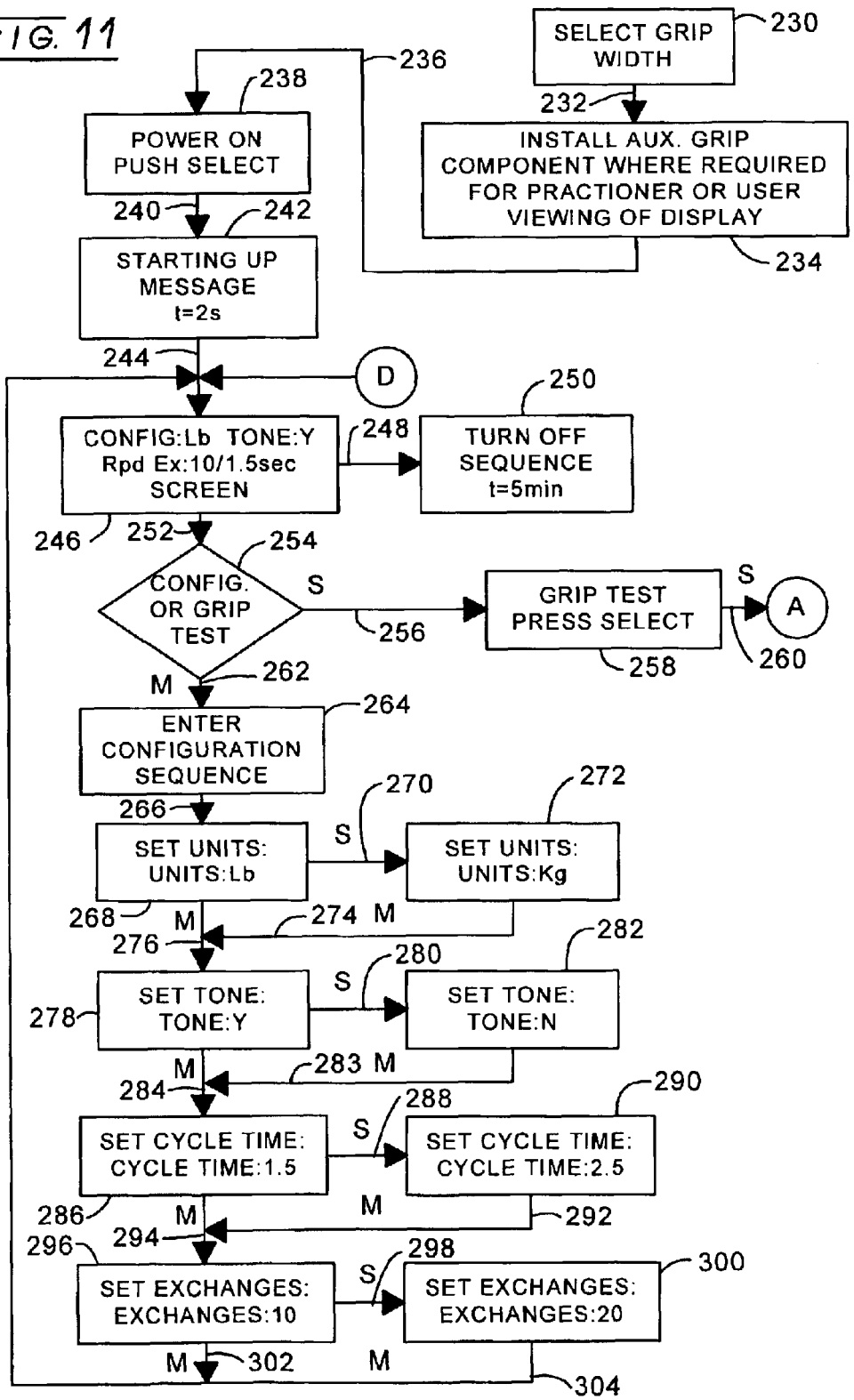
FIG. 11 is a flow chart describing the start up components of the program of the instrument of FIG. 1 as well as a configuration routine.

Turning to FIG. 11, the procedure seen to commence as represented at block 230 with the selection of the grip widthwise extent. In general, that grip width is elected to accommodate variations in user hand sizes. The program then continues as represented at line 232 and block 234 wherein, where appropriate, one or two auxiliary grip components as at 34 and 36 are installed in an orientation providing for user viewing of display 18 as illustrated in connection with FIG. 1, or in an arrangement for therapeutic practitioner viewing to the exclusion of the user as described in connection with FIG. 2. The program then continues as represented at line 236 and block 238 providing for the enablement of instrument 10 by actuation of select switch 24. Upon such actuation, as represented at line 240 and block 242 a start-up message is provided at display assembly 18 for an interval of two seconds. Then, as represented at line 244 and block 246 a prompt is displayed at readout 18 identifying a default configuration wherein pounds as opposed to kilograms are elected; an audible tone is enabled, and for a diagnostic test referred to as "rapid exchange" wherein instrument 10 is passed from one hand of the user to the other and then back for a number of exchanges, the user providing a grip force trial at each exchange. The rapid exchange default values are ten exchanges with 1.5 seconds available for user griping or squeezing. Following the publication of the screen as represented at block 246, should the user not actuate either the switches 22 or 24, then as represented at line 248 and block 250 the instrument 10 will turn off or power down at the end of a five minute interval. This feature is always active, i.e., turning off five minutes after a last switch actuation.

With the publication of the screen as represented at block 246, then as represented at line 252 and block 254 the practitioner or user is called upon to determine whether to enter a configuration sequence or to progress to a diagnostic grip test. To enter the latter diagnostic grip test sequence, as represented at line 256 and block 258 by pressing switch 24 display 18 will prompt the user to press the select switch 24 to commence a diagnostic grip test sequence. Where the select switch 24 is actuated, then the program enters the diagnostic grip test sequence as represented at line 260 and node A.

Where a determination on the part of the practitioner or user is made to enter a configuration sequence, then as represented at line 262 and block 264 the configuration sequence is entered by actuating switch 22. As represented at line 266 and block 268 the initial configuration looks to units. Recall from block 246 that the instrument 10 defaults to a units evaluated in pounds. As represented at line 270 and block 272 by actuating select switch 24 the units parameter can be converted to kilograms instead of pounds. The program then continues upon depressing or actuating menu switch 22 as represented at either lines 274 or 276 leading to block 278. As represented at block 278, the user then is given the opportunity to delete the audible tone. In this regard, by actuating select switch 24, as represented at line 280 and block 282, the tone is deleted, display 18 showing the term "tone" in connection with the letter N.

The configuration sequence then continues as represented at either lines 283 or 284 with the actuation of menu switch 22. This actuation of switch 22 provides for the establishing of a rapid exchange diagnostic test cycle time change. As set forth at block 286 the default cycle time is 1.5 seconds. However, by actuation of select switch 24, as represented at line 288 and block 290 the operator may change the cycle time to 2.5 seconds. The program then continues by actuating the menu switch 22 as represented at either of lines 292 or 294. These lines lead to the configuration alteration represented at block 296. Recall from block 246 that the default number of exchanges for the rapid exchange diagnostic procedure is 10. However, as represented at line 298 and block 300 the operator may change the number of exchanges from 10 to 20 by actuation of select switch 24. The program then returns to line 244 by actuation of the menu switch 22 as represented at lines 302 and 304. As described in connection with block 258, line 260 and node A, the operator may elect to proceed with a diagnostic grip test.

Figure 12A:
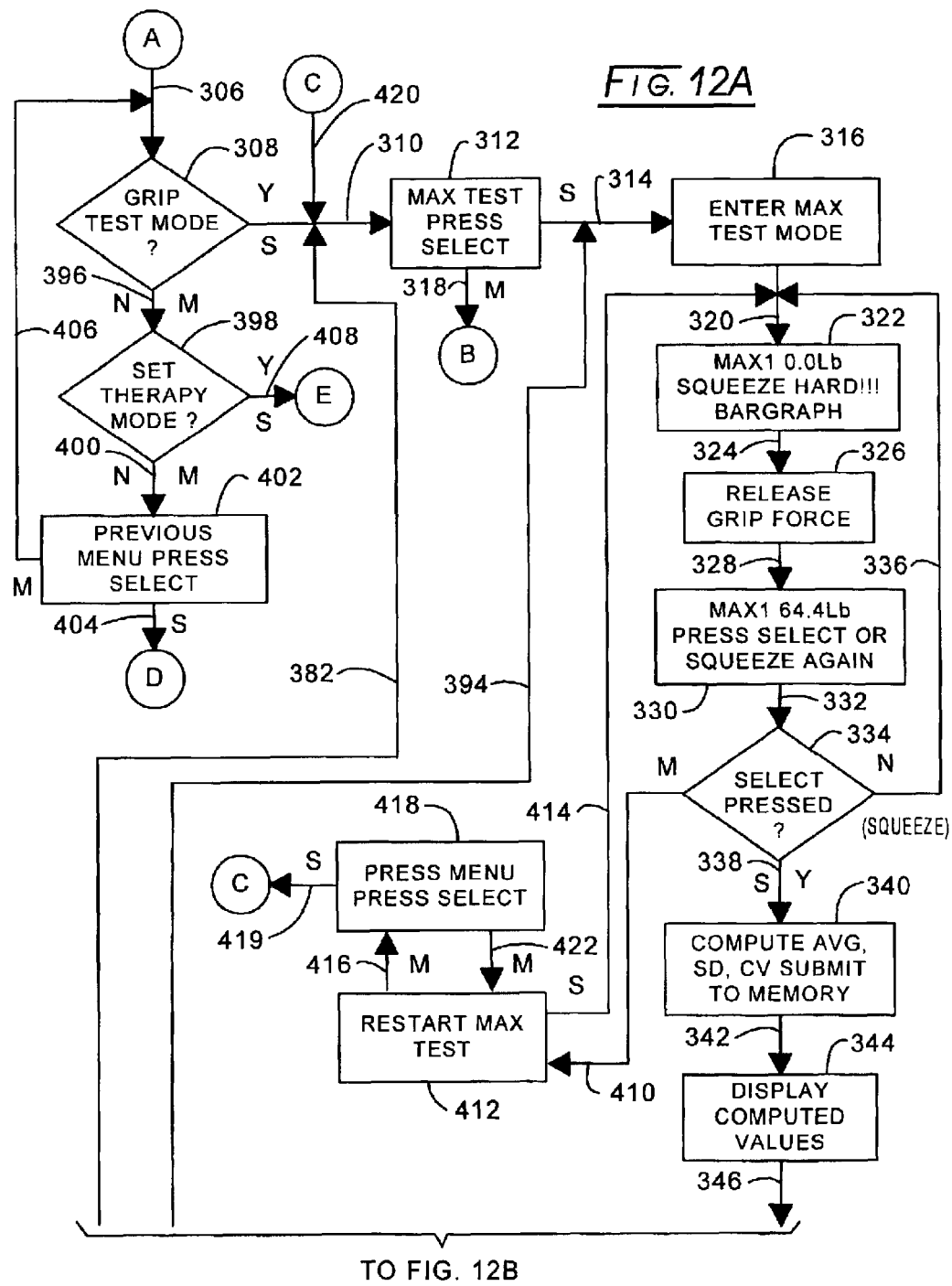

Referring to FIG. 12A, node A reappears in conjunction with line 306 extending to the query posed at block 308 wherein a determination is made as to whether or not to enter a diagnostic grip test mode. Where the operator determines that the diagnostic grip test mode should be entered, then as represented at line 310 and block 312, the grip test mode is entered by actuating select switch 24. The operator is then prompted at display 18 to actuate select switch 24 to enter a max test mode. Accordingly, with the actuation of switch 24, as represented at line 314 and block 316 the maximum diagnostic grip test mode is entered. On the other hand, as represented at line 318 and node B by actuating the menu switch 22, the practitioner may cause instrument 10 to enter a rapid exchange sequence.

Returning to block 316, the maximum strength grip test can be carried out with 10 maximum squeezing force trials. At the conclusion of a given number of such trials, the practitioner actuates select switch 24, whereupon computations are carried out. Accordingly, as represented at line 320 and block 322 the user is prompted with the message "squeeze hard!!!" at the readout 18. The program will elect the highest force applied during such squeezing activity, whereupon the user releases the grip force as represented at line 324 and block 326. Then instrument 10 will publish the maximum force applied by the user as represented at line 328 and block 330, a first maximum grip evaluation being shown as an example as 64.4 pounds. Block 330 also indicates that the user is prompted to either actuate the select switch 24 to accept the published maximum squeeze evaluation as set forth at block 330 or to squeeze the grip 14 again. Such squeezing again will provide a substitute maximum grip force evaluation. Then, as represented at line 332 and block 334 the query is posed as to whether the select switch 24 has been actuated. In the event that it has not, then the program loops as represented at line 336 extending to line 320, whereupon a maximum grip effort again is undertaken. Where the operator elects the maximum first trial grip force evaluation, then as represented at line 338 and block 340, the program will compute an average of force values, standard deviation and coefficient variation, albeit it for one trial at this juncture in the procedure.

The program then continues as represented at line 342 and block 344 to display computed values which, as noted above, for the first trial are irrelevant. However, as the number of trials increases, those computed values gain significance. Next, as represented at line 346 and block 348 the program commences to carry out a next maximum grip test by providing a prompt at readout 18 which advises the user to "squeeze hard!!!" and indicates that this is a second trial as represented by the terms: "MAX 2". Following a squeezing of the grip region 14, as represented at line 350 and block 352 the user releases the grip force and, as represented at line 354 and block 356 the maximum force asserted by the user is published, for example, showing 60 pounds for a "MAX 2" trial. This prompt further advises the user to actuate select switch 24 to elect the published grip force value or to squeeze again to carry out a next trial. The program then continues as represented at line 360 and block 362 to determine whether or not select switch 24 had been actuated. In the event that it had not been actuated then the program loops as represented at lines 364 and 346 whereupon the user again may carry out the second maximum grip trial. Where switch 24 has been actuated, then as represented at line 366 and block 368, the program carries out a computation of the average of the maximum forces asserted and computes standard deviation and coefficient of variation which are submitted to memory. The program then continues as represented at line 370 and block 372 whereupon the values computed in connection with block 368 are published at display 18. The above maximum grip test trials may be reiterated for 10 trials. Accordingly, as represented at line 374 and block 376 the maximum test trials are reiterated for a total of N tests (10 maximum) and the computed values of average force, standard deviation and coefficient of variation are both submitted to memory and published at display 18. As represented at line 378 and block 380 the user may restart this max test sequence following the Nth trial by actuating select switch 24, whereupon the program returns as represented at line 382 to line 310 (FIG. 12A). Returning to block 380, by actuating menu switch 22, as represented at line 384 and block 386, a subsequent actuation of select switch 24 will return the program to a previous menu. As represented at line 388 and block 390 by again actuating menu switch 22, as represented at line 392 the program reverts to node B as described in conjunction with FIG. 12A. By again actuating select switch 24, as represented at line 394 the program returns to entry into the maximum grip diagnostic test, line 394 extending to line 314 seen in FIG. 12A. This circular logic is made available at a variety of locations within the program.

Returning to FIG. 12A, where the query posed at block 308 results in a negative determination that the maximum grip test diagnostic mode is not to be entered, then, by actuation of menu switch 22, as represented at line 396 and block 398 a determination is made as to whether to exit a diagnostic mode and enter a therapy based mode. Where a therapy mode is not elected, then as represented at line 400 and block 402 a previous menu may be elected by actuating the select switch 24 as represented at line 404 and node D. By actuating menu switch 22, then as represented at line 406, the program loops to line 306 and the query posed at block 308. Where a therapy mode is elected by the user, then as represented at line 408, the program diverts to a therapy mode of performance as represented at line 408 and node E.

Looking back to the query posed at block 334, where the menu switch 22 is actuated as opposed to electing a maximum grip value, then as represented at line 410 and block 412 the program will reconfigure for restarting the grip test mode. Once at this point in the program as represented at block 412, by again actuating select switch 24, the program reverts, as represented at line 414 to line 320 to carry out another maximum grip trial. On the other hand, where menu switch 22 is actuated, as represented at line 416 and block 418 an indication will be given to the operator that to elect a previous menu, select switch 24 is to be actuated. As represented at line 419, the program then reverts to node C. Node C again appears in FIG. 12A in conjunction with line 420 extending to line 310. Where menu switch 22 is again actuated, the program reverts to block 412 as represented at line 422.

Looking again to FIG. 12B and the query posed at block 362, where the second maximum grip test is not selected but menu switch 22 is actuated, then as represented at line 424 and block 426 the program enters a mode for restarting the maximum grip test. By again actuating menu switch 22, as represented at line 428 and block 430 the user is prompted to enter the previous menu position in the program by actuating the select switch 24. Accordingly, by actuating switch 24 as represented at line 432, the program reverts to node C. Returning to block 426, where the select switch 24 is actuated, then the program loops as represented at line 434, to line 346 to again undertake the second of the maximum grip tests. By actuating menu switch 22 from the program location of block 430, as represented at line 436 the program reverts to its position at block 426.

Figure 13:
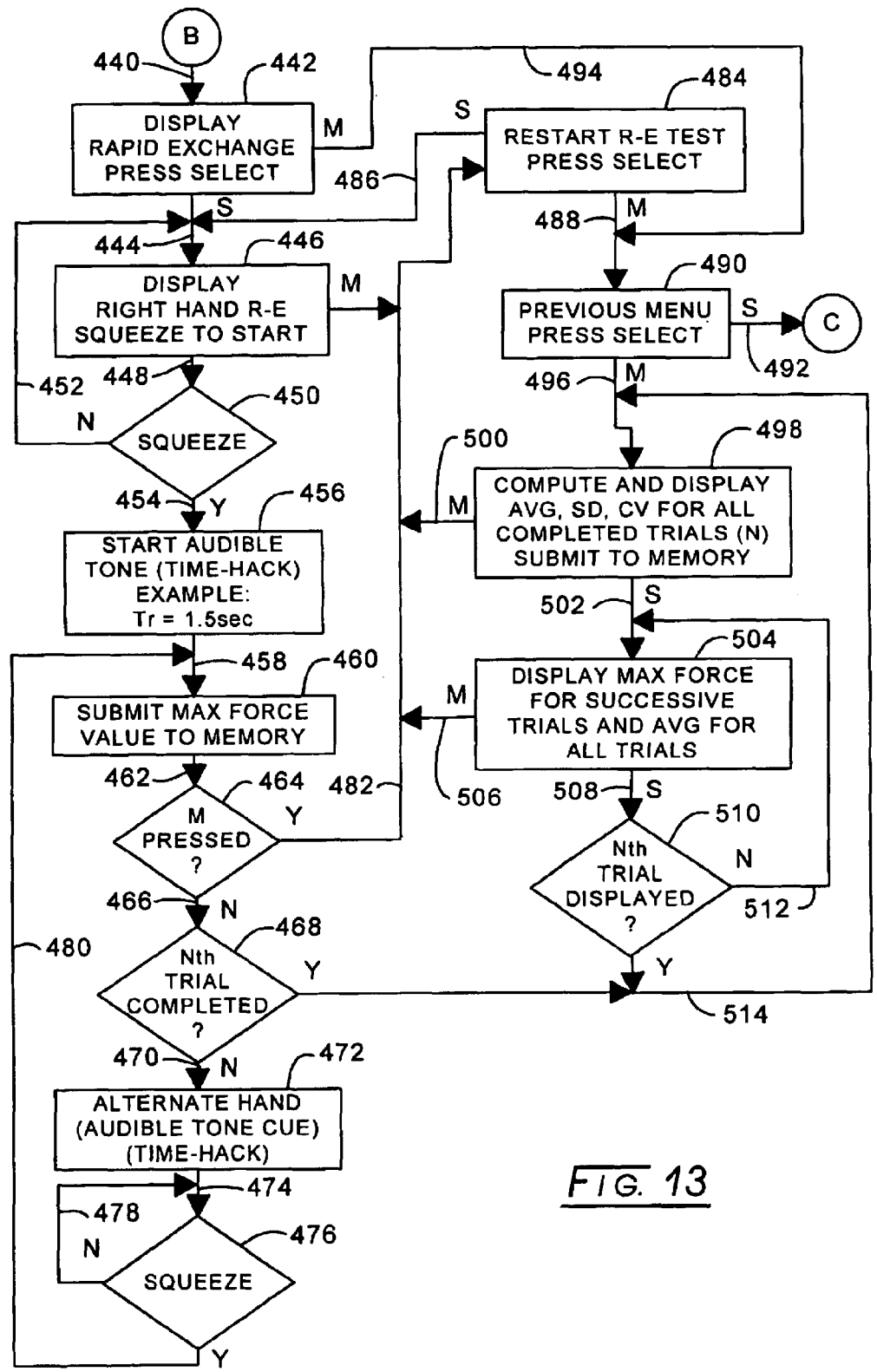
FIG. 13 is a flow chart illustrating a rapid exchange diagnostic procedure.

The diagnostic performance mode of the instrument 10 also provides for the carrying out of a rapid exchange (RE) test. With the rapid exchange test, the user may grip instrument 10 in the manner shown in FIG. 2 such that the therapist or practitioner may observe readout 18 to the exclusion of the user or patient. With the rapid exchange, a maximum grip force is exerted by the user or patient in exchanging between the right and left hands under a controlled exchange timed cycle which will have been elected, for example, in connection with the configuration mode described in connection with FIG. 11. It may be recalled that the number of exchanges may also be elected by the diagnostician as 10 or 20 efforts or trials. The rapid exchange mode of performance is elected as represented at block 312 and line 318 extending to node B described in connection with FIG. 12A. Node B reappears in FIG. 13 in association with line 440 and block 442. Referring to that figure, block 442 is seen to provide for a prompt to the practitioner to actuate select switch 24 to enter the rapid exchange mode. Upon actuating switch 24, as represented at line 444 and block 446 a prompt is provided at readout assembly 18 advising the user to squeeze the grip 14 with the right hand to start the rapid exchange sequence. As represented at line 448 and block 450 the program awaits the presence of a right hand squeezing force. Until that squeezing force is asserted, the program dwells as represented at loop 452 extending to line 444. Where a squeezing force is detected, then as represented at line 454 and block 456 the program commences to time out the succession of periods or time-hacks allocated for this cycle of the rapid exchange diagnostic procedure. That time interval may have been elected in the configuration mode as described in conjunction with blocks 286 and 290 (FIG. 11). For example, the cycle time, $T_r$ has a default value of 1.5 seconds or the last value selected.

As represented at line 458 and block 460 the user will have squeezed the grip region 14 and the maximum hand force value evolved will be submitted to memory. Then as represented at line 462 and block 464 a determination is made as to whether the menu switch 22 has been actuated. In the event that it has not, as represented at line 466 and block 468 the program determines whether the Nth, i.e., $10^{th}$ or $20^{th}$ trial has been completed. In the event that it has not, then as represented at line 470 and block 472 the rapid exchange test has not been completed and an audible tone cue (time hack) is provided indicating that the instrument should be switched to the opposite hand. A short dwell occurs as represented at line 474 and block 476 wherein the instrument determines whether or not a squeeze force has been asserted. In the event that it has not, then the program loops as represented at line 478. Where the user has imparted a squeezing force to the instrument, the program continues or loops as represented at line 480 extending to line 458 leading to a next trial in an alternate hand.

Returning to block 464 where menu switch 22 is actuated in the course of carrying out rapid exchange trials, an affirmative determination will be made with respect to the query posed at that block. Accordingly, as represented at line 482 and block 484 the user is prompted to restart the rapid exchange test by actuating select switch 24. Where select switch 24 is actuated, then as represented at line 486 the program reverts to line 444 and block 446. On the other hand, where menu switch 22 is actuated, then as represented at line 488 and block 490 the user is prompted to revert to the previous menu by actuating select switch 24. Where select switch 24 is so actuated, then the program reverts to node C as represented at line 492. Note, additionally, that if menu switch 22 is actuated in conjunction with the prompt provided at block 442, then as represented at line 494 the program reverts to line 488. Returning to block 490, where menu switch 22 is actuated then as represented at line 496 and block 498 the program computes and displays the overall average of the maximum trial values, standard deviation and coefficient of variation for the N trials. That data is submitted to memory. Should menu switch 22 be actuated at this juncture, then as represented at lines 500 and 482, the program returns to block 484. Where the select switch 24 is actuated, however, as represented at line 502 and block 504 the maximum force value for trial N and the average SD and CD for all trials is displayed. On the other hand, where the menu switch 22 is actuated, then as represented at lines 506 and 482, the program reverts to block 484.

Where the select switch 24 is actuated repetitively, then as represented at line 508 and block 510 the succession of trials 1 through N is displayed. Additionally, the unchanging average for all those trials is displayed for convenience. Further, a query is posed as to whether the Nth trial has been displayed. Where it has not, then the display program loops as represented at line 512 extending to line 502. On the other hand, where the Nth trial has been displayed, then as represented at line 514, the program loops to line 502 to repeat the succession of displays.

Figure 14A:
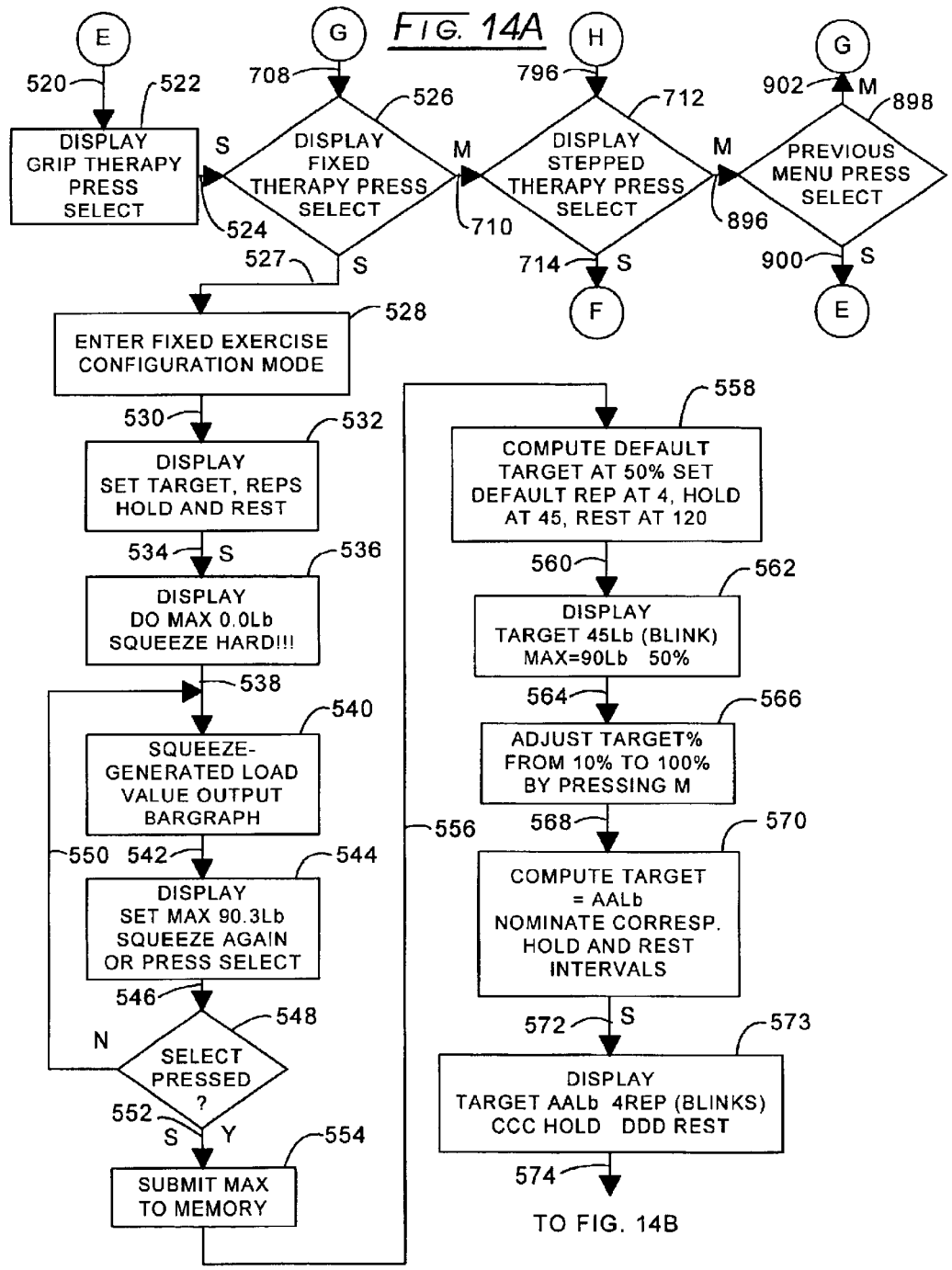

It may be recalled that in conjunction with block 398 in FIG. 12A, a therapy mode may be entered by actuation of select switch 24 as discussed in connection with line 408 and node E Node E reappears in FIG. 14A in conjunction with line 520 and block 522. Block 522 indicates that the readout 18 will publish information that a grip therapy is available by actuation of select switch 24. It may be recalled that the parameters of time and force are somewhat pre established under the regimen of the instant program. In this regard, it is important that the isometric grip exercise be constrained within predefined force and time interval of holding and resting limits. These parameters are nominated in the program and while some variations are permitted, those variations are retained within physiologically determined limit values. Of importance of the grip therapy at hand, it may be observed that it is predicated upon the patient or users actual and unique maximum gripping force which initially is evaluated and then treated by a preordained but still electable target valuation. In general, the prompts and cues provided at display 18 are made available to the patient or user by a handle configuration as described in conjunction with FIG. 1. Looking to FIG. 14A, block 522 provides for a display at readout 18 indicating that a grip therapy mode is available by actuation of select switch 24. As represented at line 524 and block 526 a determination is made as to whether a fixed mode of therapy or a stepped mode of therapy is to be elected. A fixed therapy is elected by actuation of select switch 24 as represented at line 527 extending to block 528. Block 528 indicates that the fixed exercise configuration mode has entered. With such entry, as represented at line 530 and block 532 readout 18 prompts that the user will be given opportunities to adjust the target load factor, the number of repetitions of trials of the grip therapy, the duration of the holding of the grip force at a target value and the interval for a intergripping rest. However, as an initial component of the procedure, the maximum grip force value for a given patient is determined. Accordingly, upon actuating switch 24 as represented at line 534 and block 536 the user is prompted to squeeze the grip with maximum force by publishing the terms: "squeeze hard!!!". Then, as represented at line 538 and block 540, the squeeze generated load or force value is outputted to the microprocessor 180 (FIG. 10). The maximum valuation of this initial force evaluation then is displayed at readout 18 as represented at line 542 and block 544. In the latter block, it may be observed that a sample force valuation of 90.3 pounds is published at readout 18. The user can elect that valuation as the maximum force value to be used in the program by actuating select switch 24 as represented at line 546 and block 548. However, a prompt at readout 18 also provides that the user may retry this maximum grip force evaluation as represented at loop line 550 extending to line 538. Where the user or therapist determines that an appropriate grip force has been derived, then as represented at line 552 and block 554 the elected maximum force value is submitted to memory and the program continues as represented at line 556 and block 558. employing the elected maximum squeeze force, the program computes a target grip force using a default factor of 50%. Additionally, the program establishes a trial repetition number at a default number of 4; a hold on target force interval of 45 seconds; and a default rest interval of 120 seconds. As represented at line 560 and block 562 the computed target level then is displayed at readout 18 along with the value of the elected maximum grip force and the default target factor of 50%. The terms "Target 451$b$" blink as a prompt that the factor can be altered within an established range. The user or practitioner then is given the opportunity to adjust the target factor percentage in 10% increments from 10% to 100% as represented at line 564 and block 566 by actuating the menu switch 22. Next, as represented at line 568 and block 570 the program computes at a new target value based upon the elected factor, an arbitrary designation "AA" being shown. A lower enabling grip force threshold also is derived. Should the user elect a target factor other than the 50% value by adjustment in connection with block 566, the program will automatically nominate hold on target intervals and rest intervals for each available 10% selection from within the range from 10% to 100% which the user may have elected. This, again, is for the purpose of protecting the user from excessive effort intervals and inadequate rest intervals. However, still within the mandated overall ranges, the user or therapist can change those values for the hold on target effort and rest effort. The nominated hold or "Effort" and rest intervals contained in the program are summarized in Table 1 below.

TABLE 1

| 10% Max | 20% Max | 30% Max | 40% Max | 50% Max | 60% Max | 70% Max | 80% Max | 90% Max | 100% Max |
|---|---|---|---|---|---|---|---|---|---|
| 120 sec. Effort | 120 sec. Effort | 90 sec. Effort | 60 sec. Effort | 45 sec. Effort | 15 sec. Effort | 12 sec. Effort | 10 sec. Effort | 5 sec. Effort | 3 sec. Effort |
| 60 sec Rest | 120 sec Rest | 120 sec Rest | 120 sec Rest | 120 sec Rest | 120 sec Rest | 120 sec Rest | 60 sec Rest | 60 sec Rest | 60 sec Rest |

Following the target load computation, as represented at line 572 and block 573 the program displays the newly computed target force value at readout 18 along with the default values for number of repetitions (which defaults at 4), and the nominated hold on target interval and the rest interval (Table 1). As a prompt, the readout "4 REP" blinks to indicate that adjustment is available to the user. The program then continues as represented at line 574 which reappears in FIG.

14B extending to block 576 which provides for adjusting the number of repetitions between the values 1 and 10 by actuating menu switch 22. Note that the maximum number of repetitions made available to the user is 10. The program then continues by actuating switch 24 as represented at line 578 and block 580 indicating that the computed target force level (AA) and the newly elected repetition number herein represented as "B" is provided at the display along with the nominated values for hold on target interval (CCC) and rest interval (DDD). In this display, the terms: "CCC HOLD" blink to prompt the user to make any desired adjustments within the mandated limits of from 5 seconds to 120 seconds. Accordingly, as represented at line 582 and block 584 the user or practitioner may adjust the hold on target interval by actuating menu switch 22. When the desired hold on target interval has been displayed at readout 18, the select switch 24 is actuated and the program progresses as represented at line 586 and block 588 to provide a display at readout 18 which indicates the computed target force level AA; the elected repetition number (B) and the elected hold on target interval (CCC). The display also will blink the terms "DDD REST" to prompt the user to adjust the rest interval to a desired value within the mandated interval range of 10 seconds to 120 seconds. Accordingly, as represented at line 590 and block 592 the user or practitioner can adjust (by decade components) the extent of the rest interval by actuating menu switch 22 until a desired interval value is displayed. Once the desired interval is so displayed, an actuation of select switch 24 will enter it into memory. Next, as represented at line 594 and block 596 the program displays the now elected values including the target force (AA1b); repetitions (B REP); the hold on target interval (CCC); and the rest interval (DDD). The program then provides a prompt to the user to start the therapy by actuating the select switch 24 as represented at line 598 and block 600. Upon such actuation of switch 24, as represented at line 602 and block 604 the program prompts the user at readout 18 to apply a gripping force at the target level along with the further prompt "squeeze". Next, as represented at line 606 and block 608 the program determines whether the grip force applied by the user is within 10% of the computed target force value (AA). This is the lower threshold determination as described in conjunction with block 570. In the event that the applied gripping force is not within 10% of the computed target value, the program loops as represented at line 610 extending to block 604 providing for a continuation of the prompt to hold on target. Where the applied grip force is within 10% of the computed target force value, then as represented at line 612 and block 614 the program commences to time out the hold on target interval previously elected or nominated (CCC) as discussed in connection with block 584. While this hold on target force interval is underway, as represented at line 616 and block 618 a dynamic comparison value computation is carried out over a sequence of short time components within the hold time out interval. That comparison value is utilized in driving a bar graph form of display functioning to cue the user as to a proper grip force level. During this hold interval, as represented at line 620 and block 622 the program also compares the applied grip force with a force upper limit which is computed as 125% of the target force. In the event that the applied grip force is above that upper limit, then as represented at line 624 and block 626 an audible cue is sounded to warn the user that excessive force is being applied which is outside the proper protocol for the therapy. The program then continues as represented at lines 628 and 630 whereupon as set forth at block 632 a score as a percentage of target value is computed for a sequence of time increments. This score may be utilized by the user and the therapist for purposes of evaluating the quality of the exercise regimen carried out by the user.

Figure 15:
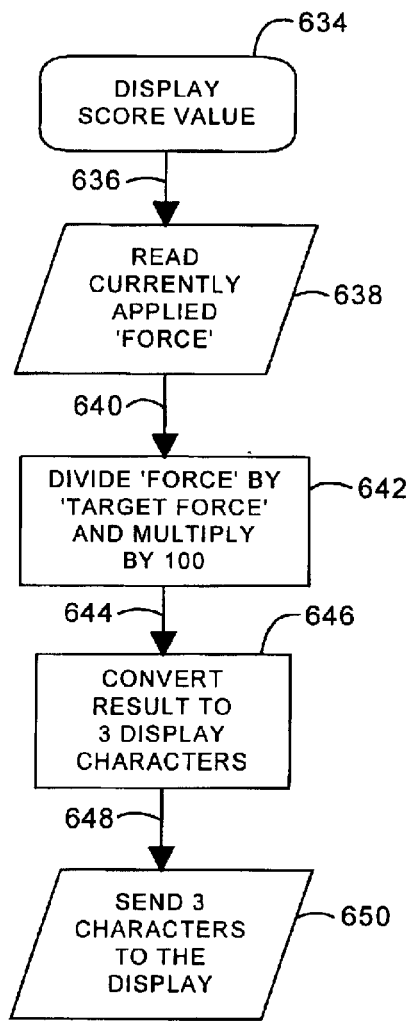
FIG. 15 is a flow chart demonstrating the technique by which a score value is developed by the apparatus of the invention.

Turning momentarily to FIG. 15, a routine is depicted functioning to carry out the computation and display of the noted score values. This routine is entered into as represented at node 634 identifying it as a display of the score value. The routine commences as represented at line 636 and block 638 indicating that the currently applied grip force or load value is read as the user attempts to match the target force value. Then, as represented at line 640 and block 642, the score is determined by dividing that read force by the pre-computed target force and multiplying the result by 100 to provide the score as a percent. This score is developed for sequential increments of time, preferably each increment representing 1% of the hold on target interval (CCC). As represented at line 644 and block 646, the score is converted into three display characters. Then, as represented at line 648 and block 650, three characters representing the score are sent to readout 18 for display. The score may be above or below 100%, 100% representing an on target grip force.

Returning to FIG. 14B, the program continues as represented at line 652 which reappears in FIG. 14C extending to block 654. Block 654 indicates that a display is provided at readout 18 which cues the user as to essentially instantaneous score value, the time remaining for holding on target and further cues the user as to the level of grip force being applied with respect to target through the utilization of a center pointer visual cue representing the target load value and an effort dynamic bar graph visual cue having a top position present as a bar graph top line. That top line will be aligned with the center pointer when the load value at output represents a force equal to the target load value. The top line will move away from the center pointer when the load value output or grip force exerted by the user represents a force which deviates from the target load value.

Figure 16E:
FIGS. 16A–16E are a sequence of displays provided by the instrument of the invention showing a publication of score, a dynamic bar graph with center pointer and a time remaining cue.
Figure 16D:
Figure 16C:
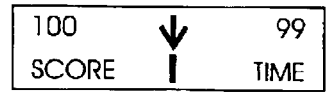
Figure 16B:
Figure 16A:
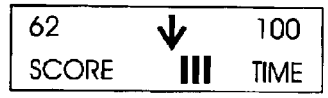

Looking momentarily to FIGS. 16A–16E, a representation of the display so provided for differing grip force activity is set forth. In FIG. 16A, the dynamic bar graph extends to the right of the center pointer indicating a grip force which is too low. This lower grip force also is indicated by the lower score value of 62%. The display also includes an indication of the time remaining for the hold on target interval, for example, 100 seconds. FIG. 16B also indicates through the dynamic bar graph that the asserted grip force is still too low but improved over that shown in FIG. 16A as indicated by the shorter extent of the dynamic bar graph to the right of the center pointer and a higher score value of 75%. FIG. 16C shows a cue wherein the user grip force is at the target force, the top line of the bar graph being aligned with the center pointer and a score of 100% being displayed. Additionally, as before, the time remaining for the hold on target interval is displayed. FIG. 16D shows that an excessive grip force is being applied by the user, the dynamic bar graph extending to the left of the center pointer. This excessive force also is indicated by a score value of 125%. Time remaining in seconds within the hold on target interval also is displayed. Finally, FIG. 16E shows a still more excessive application of grip force on the part of the user, the dynamic bar graph top line extending well to the left of the center pointer and a score of 137% being represented. As before, time remaining in the "on target interval" is also displayed.

Returning to FIG. 14C the program is seen to continue as represented at line 656 and block 658 wherein a query is made as to whether the hold on target interval has timed out.

In the event that it has not, then the program dwells as represented by loop line 660 extending to node I which reappears in FIG. 14B with line 662 extending to line 620. In the event of an affirmative determination with respect to the query posed at block 658, then as represented at line 662 and block 664 an audible cue is generated at the annunciator 198 (FIG. 10). With the generation of this audible cue, then as represented at line 666 and block 668 the rest interval commences to be timed out. It may be recalled that the rest interval was elected in conjunction with block 592 (FIG. 14B). During this rest interval, as represented at line 670 and block 672 the program will provide a display at readout 18 which indicates the number of trials or efforts remaining in conjunction with the elected repetition value. At the termination of the first trial, that value will be B−1. The display also provides the average value of score and the interval of time remaining in the rest interval. Next, as represented at line 674 and block 676 a query is made as to whether the rest interval has timed out. In the event that it has not, then the program dwells as represented at loop line 678. Where the query posed at block 676 results in an affirmative determination, then as represented at line 680 and block 682 an audible cue is generated and the program continues as represented at line 684 and block 686 providing for a reiteration of the trial sequence. As represented at line 688 and block 690 a query is made as to whether the elected number of repetitions of the trial (B) has been accomplished. In the event that that elected number of repetitions has not been completed, then the program dwells as represented at line 692. In the event of an affirmative determination with respect to the query posed at block 690, then as represented at line 694 and block 696 a final or average score is computed and submitted to archival memory in conjunction with calendar and force data. In the latter regard, each of the average grip force values asserted by the user for each trial are recorded. Next, as represented at line 698 and block 700 the program determines or selects an appropriate message of congratulation or warning base upon the computed final score. The program then continues as represented at lines 702 and block 704 to publish the selected message at readout 18 and continues as represented at line 706 to node G.

Node G reappears in conjunction with line 708 (FIG. 14A) and block 526. Where the user or therapist has determined to cause instrument 10 to enter into a stepped therapy mode, menu switch 22 is actuated as represented at line 710 and the program displays a prompt to the user as represented at block 712 indicating that the step therapy mode may be entered by actuating select switch 24 as represented at line 714 and node F.

Referring to FIG. 17A, node F reappears in conjunction with line 716 and block 718 providing for the entry of instrument 10 into a stepped exercise configuration mode. In this therapeutic mode the maximum grip strength unique to the user or patient is determined, whereupon the therapeutic gripping regime is one wherein the target load level as well as hold on target intervals and rest intervals vary in accordance the sequence of steps or gripping trials. The program opens as represented at line 720 and block 722 with a display at readout 18 prompting that the user is to be called upon to establish a maximum grip force level and carry out a setting of the number of steps and repetitions of the therapy. The user then actuates the select switch 24 and, as represented at line 724 and block 726 the program displays a prompt at readout 18 indicating that the user should carry out a maximum grip force exercise, the prompt including the terms; "squeeze hard!!!". Then, as represented at line 728 and block 730 the user will have applied maximum squeezing force to the grip and that will have generated a load value output. While this load value output is being generated, as represented at line 732 and block 734 the program displays a cue at readout 18 which publishes the value of the maximum gripping force. Should the practitioner or user wish to attempt to improve that value, he or she is prompted to actuate select switch 24 and elect the value published or to squeeze the grip again. Where the user elects the value published, then as represented at line 736 and block 738 a determination is made as to whether the select switch 24 has been actuated. In the event that it has not, then the system dwells as represented at loop line 740 extending line 728. Where the select switch 24 has been actuated, then as represented at line 742 and block 744 the maximum gripping force value which was selected is submitted to memory and, as represented at line 746 and block 748 the system provides a 1 step default value and a repetition of the step exercise is defaulted to a value of four. The program then continues as represented at line 750 wherein the system provides a prompt at readout 18 which displays the value of a selected maximum gripping force and further prompts the user that a default of 1 step is present and a default of four repetitions is present. The term "1 step" is intermittent or blinks as a part of this prompt to the user to elect the number of steps desired. This display is represented at block 752. Then, as represented at lines 754 and block 756 the user or practitioner is permitted to adjust the number of steps within a range of 1 to 5 steps. As discussed above, this range is mandated within the system and the adjustment in the number of steps may be carried out by actuating menu switch 22.

The number of steps elected adjusts the percentage of maximum grip force factor in accordance with a preordained schedule. That schedule is provided in Table 2 below. For example, if only one step is elected, that target grip factor will be 20%. On the other hand if five steps are elected, the first trial will be at 100% of maximum grip force. The second step will be at 80% of maximum grip force and so forth. On the other hand, if four steps are elected, the initial trial will be in conjunction with an 80% maximum grip force factor; the second step will be at 60% and so forth as set forth in Table 2. For each of these percentages as set forth in Table 2, the corresponding hold on target or effort interval and rest intervals will follow the values given above in Table 1.

TABLE 2

| No. of Steps Elected | 1 | 2 | 3 | 4 | 5 |
|---|---|---|---|---|---|
| 1st Step as % Max | 20% | 40% | 60% | 80% | 100% |
| 2nd Step as % Max | | 20% | 40% | 60% | 80% |
| 3rd Step as % Max | | | 20% | 40% | 60% |
| 4th Step as % Max | | | | 20% | 40% |
| 5th Step as % Max | | | | | 20% |

The step value is elected by actuation of select switch 24 and the program continues as represented at line 758 and block 760. Block 760 replicates a display at readout 18 which prompts the user by indicating that the maximum elected gripping force selected was 90 pounds and that A steps were selected and a further prompt is provided showing blinking or intermittent display of "4 REPS". Then, as represented at line 762 and block 764 the operator may adjust the number of repetitions of the program to a value within a preordained number of 1 through 10 by actuating menu switch 22. The elected number of repetitions then is selected by actuation of switch 24 and, as represented at line 766 and block 768 the system displays the now selected parameters of a maximum grip force, for example, 90 pounds, an election of A steps in the regimen and an election of "B" repetitions. Next, as represented at line 770 and block 772 the stepped exercise therapy is entered. Upon entry into this stepped exercise trial mode, target values are computed based upon the number of steps elected and the hold on target and rest intervals will be acquired, such data with respect to target factors being set forth in Table 2 and the latter hold on target and rest intervals being set forth in Table 1. This function is represented in block 776. Line 778 reappears in FIG. 17B extending to block 780 which prompts the user with a display indicating that to start the step therapy the select switch 24 should be actuated. The operator may return the system to a previous menu at this juncture by actuating menu switch 22. In this regard, as represented at line 782 and block 784 by actuating switch 22, the program will again display that initially elected maximum 90 pound grip force along with the prompt to squeeze again or press select as represented at line 785 and node K. This returns the program to block 752 (FIG. 17A) where node K reappears at line 750. While again actuating switch 22, as represented at line 786 and block 788 a restarting of the step therapy test prompt is provided advising the user to actuate switch 24. Again where switch 22 is actuated, then as represented at line 790 and block 792 the user is provided a prompt display at readout 18 advising that the previous menu may be elected by actuating select switch 24. Where that switch is actuated, then as represented at line 794 and node H the program returns to block 712 as earlier described in connection with FIG. 14A. In this regard, node H reappears in that figure in conjunction with line 796 extending to block 712. Where menu switch 22 is actuated the program loops as represented at line 795 extending to line 782.

Returning to block 780, where switch 24 has been actuated, then as represented at line 798 and block 800 the user is prompted to hold the grip force at the computed target level for 100%. Additionally, the prompt term "SQUEEZE" is provided within the readout 18. Next, as represented at line 802 and block 804 a determination is made as to whether the grip force exerted by the user is within 10% of the computed target value. Where it is not, then the system dwells as represented at loop line 806 and the display represented at block 800 continues. Where the asserted grip force is within 10% of the target load, then as represented at line 808 and block 810 the mandated hold on target interval timeout set forth in Table 1 commences and, as represented at line 812 and block 814 a dynamic comparison value is derived for dynamic bar graph cueing. Next, as represented at line 814 and block 816 a computation then is made as to whether the instantaneous grip force is at or above 125% of the target value. Where that is the case, then as represented at line 820 and block 822 an audible warning cue is sounded. The program then continues as represented at lines 824 and 826 when the excessive force has been lessened. Line 826 is directed to block 828 which provides for carrying out a computation of a score value as a percentage of target for a sequence of time increments. Computation of this score has been discussed in connection with FIG. 15. The program then continues as represented at line 830.

Figure 17C:
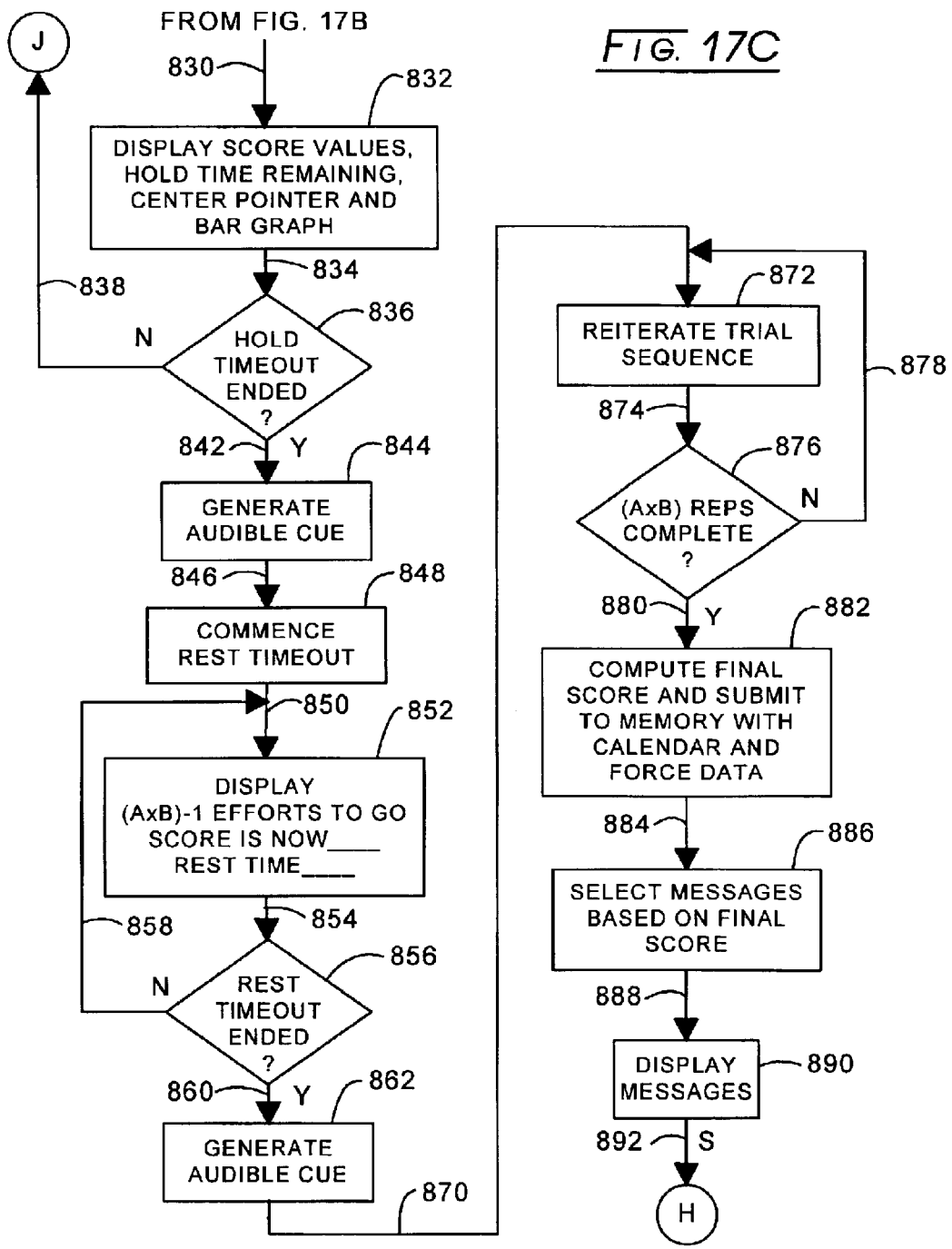

Line 830 reappears in FIG. 17C extending to block 832 which provides a display at readout 18 with essentially instantaneous score values, the noted dynamic bar graph and hold time remaining for the initial step at hand. The dynamic bar graph has been described in conjunction with FIGS. 16A–16E. Next, as represented at line 834 and block 836 a query is posed as to whether the hold time interval has expired. Where it has not, then the system dwells as represented at loop line 838 extending to node J. Node J reappears in FIG. 17B in conjunction with line 840 extending to line 816. However, where the hold on target interval has expired, then as represented at line 842 and block 844 an audible cue is generated and, as represented at line 846 and block 848 a Table 1 mandated rest interval is commenced. The program then continues as represented at line 850 and block 852 wherein the system cues the user that (A×B)−1 efforts remain out of the previously selected (A×B) efforts and further advises of the time remaining for the rest interval and the current score value. With this display, the system queries as to whether the rest interval has expired as represented at line 854 and block 856. Where the rest time remains at hand, then the system dwells as represented at loop line 858 extending the line 850. However, where the rest interval has expired, then as represented at line 860 and block 862 an audible cue is generated.

Following the generation of this audible cue, as represented at line 870 and block 872 the program reiterates the trial sequence following the mandates of Tables 1 and 2 and the elected parameters. As represented at line 874 and block 876, a query then is made as to whether the repetitions and associated efforts are complete. This value is the product of the elected number of steps A multiplied by the elected number of repetitions, B. Where that number of reiterations has not occurred, then the program continues as represented by loop line 878 extending to line 870. Where the number of repetitions is completed, then as represented at line 880 and block 882 a final score is computed and submitted to memory with calendar and force data. Next, as represented at line 884 and block 886 the program selects a message to the user which will be based upon the final score. For example, the user may be advised to consult a therapist or the program directions in the event of a low score and is congratulated in the event of a good score. As represented at line 888 and block 890 those messages are selected. Where the user actuates select switch 24, the program continues as represented at line 892 and node H.

Turning again to FIG. 14A, node H reappears in conjunction with line 796 leading to the block 712 displaying a prompt that, to cause the program to enter the stepped therapy mode, the select switch 24 should be actuated. However, where menu switch 22 is actuated, then as represented at line 896 and block 898 the program displays a prompt that to enter the previous menu, the select switch 24 should be actuated. Where that select switch is so actuated, then as represented at line 900, the program reverts to node E which reappears in the instant figure in conjunction with line 520 extending to block 522. On the other hand, where the user actuates menu switch 22, then as represented at line 902 the program reverts to node G. Node G is shown in the instant figure in conjunction with line 708 extending to block 526.

The user has the option of powering down instrument 10 by pressing select switch 24 for an interval of at least 2 seconds. This power off sequence is represented in the flow chart of FIG. 18. The sequence opens with node 910 and line 912 extending to block 914. Block 914 indicates that select switch 24 is being actuated and held in an actuated state. During this actuated state, as represented at line 916 and block 918 a determination is made as to whether the 2 second interval has elapsed. If it has not, then as represented at line 920 and block 922 a query is posed as to whether the select switch 24 has been released before the termination of 2 seconds. If it has not, the system dwells as represented at loop line 924 extending to line 916. Where the query at block 918 results in an affirmative determination, then as represented at line 926 and block 928 the instrument 10 is powered down. Where the determination at block 922 indicates that the switch 24 has been released prior to the elapsing of 2 seconds, then as represented at line 930 and block 932 the program reverts to the previous or last display which was published at readout 18.

The protocol based isometric exercise approach of the invention has applicability to a broad range of muscle groups of the user. By employing the protocol which, inter alia, involves the evaluation of maximum muscle group strength as a precondition to then applying a factor related protocol, one of those factors may apply to the measured maximum strength value. The remaining factors which involve, for example, variations of target loads, hold times, rest intervals and exercise regimen planning in terms of calendar days achieves a safe and effective utilization of isometric activities. The exercisable anatomical features to be strengthened are generally identifiable as muscle groups of the human anatomy which may include but are not limited to: jaw muscles, neck muscles, shoulder muscles, upper arm muscles, lower arm muscles, hand muscles, finger muscles, diaphragm muscles, abdominal muscles, lower back muscles, upper leg muscles, lower leg muscles, ankle muscles, foot muscles, and toe muscles.

Figure 19:
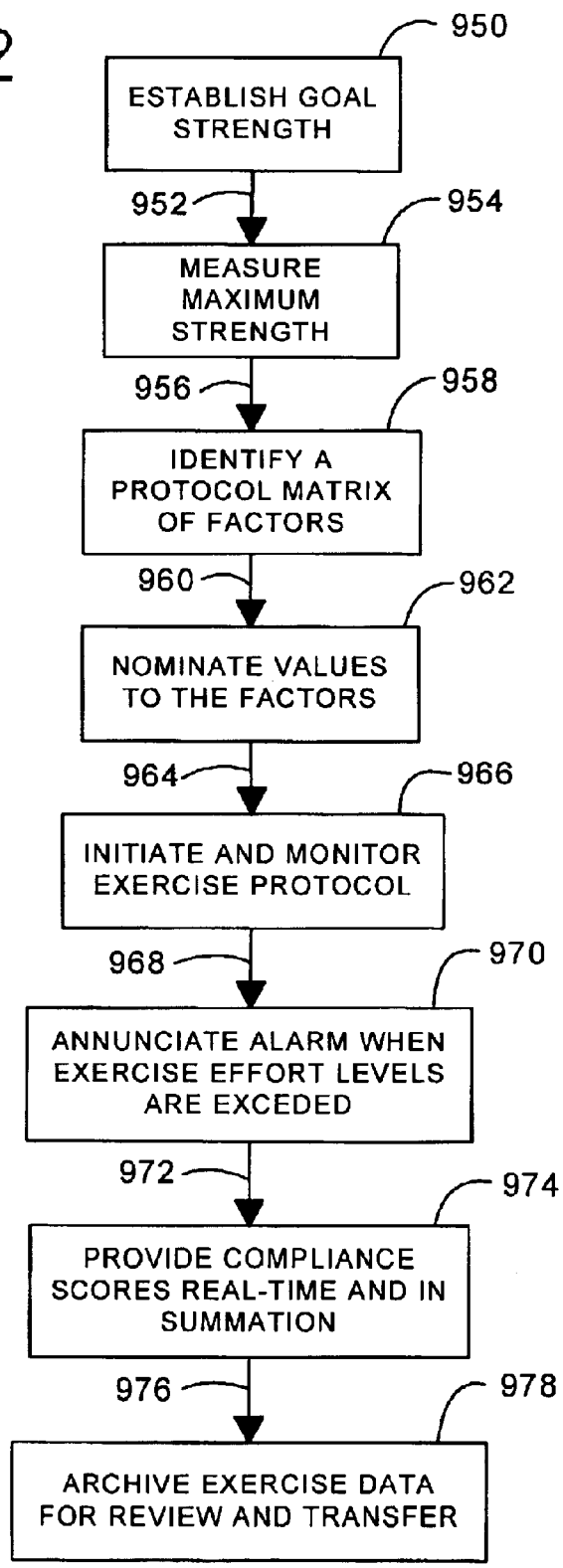
FIG. 19 is a flow chart describing the applicability of the use of isometric exercise in conjunction with safe muscle strengthening and therapy protocols for a broad range of muscle groups.

Looking to FIG. 19, a flow diagram is presented which outlines the methodology achieving this safe utilization of isometric exercises. In the figure, block 950 reveals that the user or therapist may establish a goal of strength for the muscle group involved. This may be achieved by measuring the maximum strength of an unimpaired contralateral muscle group. For example, a left arm or upper leg muscle group may be tested to determine a strength goal for a right arm or right upper leg muscle. Where no unimpaired contralateral muscle group is available to set this goal strength, a medical professional will establish an appropriate goal strength. The method continues as represented at line 952 of block 954 providing for the measurement of maximum strength of the specific anatomical feature to be treated. As represented at line 956 and block 958, the methodology identifies a protocol matrix of factors. In this regard, a strengthening protocol is derived which is based upon timed efforts which are equal to a percentage of the measured maximum strength as derived in connection with block 954. The matrix of factors further include hold times at a factor or factors of the measured maximum strength, the repetition of these efforts for a given trial or exercise session and the duration of rest periods where repetitions are involved. Such protocol further will indicate the intervals of repetitions of the exercise sessions themselves during a stated period of time in hours, days, weeks, months and the like. This matrix of factors may be contained, for example, in computer memory. Looking to line 960 and block 962, the procedure next nominates values to the factors provided in conjunction with block 958. In this regard, the strengthening protocol which is developed utilizes nominated factors from the matrix of these exercise factors. In effect, the nominated factors may be identified as "effort" applied by the specific anatomical feature and the effort time period during which the effort is to be applied such that there is a relationship among the percentage of the measured maximum strength of time wherein the higher the percentage, the shorter the effort time and the number of repetitions of these efforts during an exercise session, the rest period time between cessation of one effort and the beginning of the next succeeding effort such that there is a relationship between the percentage of the measured maximum strength and the rest time wherein the higher the percentage the longer the rest time and the number of exercise sessions in a given time period (hours, days, weeks, months). As represented at line 964 and block 966, the procedure initiates and monitors the exercise protocol with nominated factors. In this regard, the procedure monitors and guides the exercise effort to be applied and while being applied, provides visual and/or audible cues to encourage compliance to the elected protocol using symbols as the visual cues and words which clearly guide the effort to be applied. While that effort is being applied, using audible cues and words which assist to properly perform the effort, rest periods and repetitions for each exercise session. Looking to line 968 of block 970, the method provides for annunciating an alarm when an exercise effort level is exceeded. In this regard, an audible alarm is produced if the exercise effort exceeds a predetermined or factor determined level beyond which it is considered that the exercise effort could be damaging to the human physiology or the specific anatomical feature at hand. As represented at line 972 and block 974 the method provides compliance scores in real-time and in summation during the course of an exercise effort and subsequent thereto. As described herein, the program calculates a compliance score during each exercise effort in percent of that effort required in the strengthening protocol and provides this compliance score in real-time as the effort is being accomplished on the specific anatomical feature. An averaging of this compliance score over each exercise effort time period is devised to depict the degree to which the exercise effort applied has been accomplished. By accumulating the compliance scores during each rest period and then presenting a final compliance score issued in the form of both a number as a percent accomplished and in an instruction set an indication is derived as to how well the exercise protocol was performed or how to improve future compliance. Next, as represented at line 976 at block 978 the exercise data is archived for review and potential transfer to a remote interactive entity. This step in the procedure accumulates real-time and summary data for each effort or trial and the specific protocol being utilized. It may be noted that these protocols are selected each time the exercisable anatomical feature is elected to be strengthened such that the elected protocol, the effort being applied and the compliance being calculated during and at the conclusion of each effort may be reviewed remotely as it is being accomplished using suitable data communication assistance and at the conclusion of each effort. The archive data is time-stamped and uniquely identified for retrieval.

Since certain changes may be made in the above-described apparatus, method and system without departing from the scope of the invention herein involved, it is intended that all matter contained in the description thereof or shown in the accompanying drawings shall be interpreted as illustrative and not in a limiting sense.

What is claimed is:

1. A system for carrying out an isometric diagnostic regimen by a user, comprising:

a hand grip assembly including a load cell component responsive to compressive squeezing force applied by a hand of the user to derive a load value output corresponding with the value of said force;

a display, responsive to a visual input signal to provide a visually perceptible display output;

first and second control members hand actuateable to provide respective first and second control conditions;

a controller including a processor and a memory operatively associated therewith and controllable to enable said processor and memory; and said processor, when enabled, entering a grip test mode wherein the processor is responsive to said first control condition to enter a maximum test mode to derive a visual input signal providing a first cue to said user to squeeze said hand grip with a maximum force capability, is responsive in the presence of said first cue and a first load value output occurring for a finite interval to derive said visual input signal providing a second cue displaying a first value of force corresponding with said first load value output, responsive to said first control condition in the presence of said second cue to enter said first value of force into said memory defining a maximum grip test, responsive to a subsequently occurring first control condition to derive a visual input signal providing a next occurring said first cue, responsive in the presence of said next occurring first cue and a second load value output occurring for a finite interval to derive a visual input signal providing a next said second cue displaying a second value of force corresponding with said second load value output, responsive to said first control condition in the presence of said next second cue to enter said second value of force into said memory defining another said maximum grip test, responsive to carrying out a mathematical analysis of said first and second values of force, and to derive a visual input signal providing a third visual cue displaying the results of said mathematical analysis, said processor being responsive in said grip test mode, in the presence of said visual input signal providing said second cue displaying said first value of force, and in the absence of said first control condition, to a next occurring said load value output occurring for a finite interval to derive a visual input signal providing a second cue displaying a substitute said first value of force corresponding with said next occurring load value output, and is responsive to said first control condition in the presence of said second cue displayed substitute first value of force to enter said substitute first value of force into said memory.

2. The system of claim 1 in which:
said processor is responsive in said test grip mode to said first control condition in the said presence of said second cue displayed substitute first value of force to enter the greater of said first value of force or said substitute first value of force into said memory.

3. The system of claim 1 in which:
said processor is responsive when in said grip test mode to an actuation of said second control member and resultant said second control condition to restart said grip test mode providing for said response to said first control condition to enter said maximum test mode.

4. The system of claim 1 in which:
said processor, when enabled, is responsive to said second control condition to enter a configuration mode wherein said visual input signals, are electable by subsequent actuation of said first and second control members.

5. The system of claim 1 in which:
said processor, when enabled is responsive to said second control condition to enter a configuration mode wherein the number of said maximum grip tests to be carried out when in said grip test mode is electable by subsequent actuation of said first and second control members.

6. A system for carrying out an isometric diagnostic regimen by a user, comprising:
a rigid housing;
a handgrip assembly integrally formed with said housing, including a load cell component responsive to compressive squeezing force applied by a hand of said user to derive a load value output corresponding with the value of said force;
a display supported by said housing, responsive to a visual input signal to provide a visually perceptible display output and to an audible input signal to provide an audibly perceptible cue output;
first and second control members supported by said housing, hand actuateable to provide respective first and second control conditions;
a controller mounted within said housing, including a processor and memory operationally associated therewith; and
said processor, when enabled, being responsive to said second control condition to enter a rapid exchange test mode to carry out an alternating user hand sequence of N maximum squeezing force trials at a timed repetition rate of period $t_r$, effective for carrying out a rapid exchange test responsive to said first control condition to derive a visual input signal providing a starting trial prompt, is responsive to an initial load value output generated with one hand of said user to derive a visual input signal providing a force value cue and is responsive to time an initial said period $t_r$ and to derive an audible input signal at the timeout of period, $t_r$, and enter the value of said force corresponding with said initial load value output to into memory, and responsive to reiterate the derivation of visual input signal, timing of period, $t_r$, in response to timeout of the next previous period $t_r$, and the derivation of a corresponding visual input signal providing a force value cue, generating said audible input signal at the timeout of period $t_r$, and entry of a value of force corresponding with said load value into memory for a total of N trials, and responsive at the termination of the Nth trial to compute the average value of force, standard deviation and coefficient of variation for N trials, responsive to derive a visual input signal corresponding with said computed average value of force, standard deviation of memory retained force values and the corresponding coefficient of variation for N trials.

7. The system of claim 6 in which:
said processor is responsive to commence the timing of said initial period, $t_r$, upon the initiation of said initial load value output.

8. The system of claim 6 in which:
said processor is responsive at the termination of each said period, $t_r$, for each said trial, to compute the average value of force, standard deviation and coefficient of variation with respect to all trials theretofore carried out and enter said value of force corresponding with the termination of each said period, $t_r$, and corresponding said average value of force, standard deviation and coefficient of variation into said memory.

9. The system of claim 8 in which:
said processor is responsive, upon the termination of the Nth trial to initiation of a said first control condition to derive a visual input signal providing a display output of force value corresponding with said initial value output, is responsive to subsequent successive initiation of said first control condition to derive visual input signals providing display outputs of memory retained force values, and computed average value of force, for each corresponding successive trial.

10. The system of claim 6 in which:
said processor is responsive to time said initial period $t_r$ commencing with initiation of said initial load value output.

11. A system for carrying out an isometric exercise regimen by a user, using a single hand, comprising:

a handgrip assembly including a load cell component responsive to compressive squeezing force applied by a hand of the user to derive a load value output corresponding with the value of said force;

a display, responsive to a visual input signal to provide a visually perceptible display output;

first and second control members hand actuateable to provide respective first and second control conditions;

a controller including a processor and memory operationally associated therewith, and, said processor, when enabled, being responsive to said first control condition to enter a fixed exercise configuration mode and derive a visual input signal providing a first prompt to the user to squeeze said handgrip assembly at maximum capability, responsive to said load value output to derive a visual input signal providing a first cue displaying the maximum force value corresponding with said load value output, responsive to a first control condition to enter said maximum force value into memory, responsive to a first control condition to derive a visual input signal providing a second prompt to enter a desired target load factor, responsive to said second control condition to derive a desired target load factor, responsive to said desired target load factor and said memory retained maximum force value to compute a target load value and enter the target load value into memory responsive to said first control condition to derive a visual input signal providing a third prompt to enter a desired trial repetition number, responsive to a second control condition to derive a desired trial repetition number for entry into memory, responsive to said first control condition to derive a retained maximum force value to compute a target load value and enter the target load value into memory, responsive to said first control condition to derive a visual input signal providing a fourth prompt to enter a desired target load hold interval, responsive to a second control condition to derive a desired target load hold interval for entry into memory, responsive to said first control condition to derive a visual input signal providing a fifth prompt to enter a desired inter-trial rest interval, responsive to a second control condition to derive a desired inter-trial rest interval for entry into memory, responsive to said first control condition to derive a visual input signal providing a sixth prompt to the user to commence a trial by applying squeezing force to said handgrip assembly at said target load value, responsive in the presence of a load value output to time-out said memory retained desired target load hold interval, to derive a score value based upon the memory retained target load value and said load value output and to derive a comparison value representing the generally instantaneous relationship between target load value and the value of force corresponding with the load value output, responsive to derive a visual output signal providing a second cue to the user representing said comparison value, said score value and the status of said time-out of the hold interval, responsive at the termination of the target load hold interval to time-out the desired inter-trial rest interval and to derive a visual input signal providing a seventh prompt to the user of the presence of said inter-trial rest interval, and responsive at the termination of said inter-trial rest interval, to said desired trial repetition number to reiterate commencement of a trial by deriving the sixth prompt.

12. The system of claim 11 in which said processor is responsive when in said fixed exercise configuration mode to said second control condition to enter a derived target load factor from within a permissible load range from about 10% to about 100%.

13. The system of claim 12 in which:

said processor is responsive when in said fixed exercise mode to nominate a memory retained predetermined value for said target load hold interval, and is responsive when in said fixed exercise mode to enter said predetermined value for said target load hold interval as said desired target load hold interval in the absence of said second control condition.

14. The system of claim 12 in which:

said processor is responsive when in said fixed exercise mode to nominate a memory retained predetermined value for said inter-trial rest interval; and is responsive when in said fixed exercise mode to enter said predetermined value for said inter-trial rest interval as said desired inter-trial test interval in the absence of said second control condition.

15. The system of claim 11 which said processor is responsive when in said fixed exercise configuration mode to said second control condition to enter a desired trial repetition number from within a permissible repetition number range from about one to about ten.

16. The system of claim 11 in which:

a default target load factor of about 50% is retained within said memory; and said processor is responsive when in said fixed exercise configuration mode to enter said default target load factor as said desired target load factor in the absence of said second control condition.

17. The system of claim 11 in which:

a default trial repetition number of about four is retained within said memory; and said processor is responsive when in said fixed exercise configuration mode to enter said default trial repetition number as said desired trial repetition number in the absence of said second control condition.

18. The system of claim 11 in which said processor is responsive to a load value output representing a predetermined percentage of computed target load value to effect commencement of time-out of the desired target load hold interval.

19. The system of claim 11 in which:

said controller includes a calendar circuit deriving a date output; and said processor is responsive to said date output to effect the recordation thereof in said memory in conjunction with said maximum force value and said score value.

20. The system of claim 19 in which:

said controller includes a data transfer port connectable with an interactive data communication system; and said processor is responsive to an input from said interactive data communications system to download said date output, said maximum force value and said score value.

21. The system of claim 11 in which:

said processor is responsive to said comparison value to derive a visual output signal providing said second cue as including a center pointer visual cue representing target load value, and an effort dynamic bar graph visual cue having a top position present as a top line aligned with the center pointer when the load value output represents a force equal to said target load value, the top line moving away from the center pointer when the load value output represents a force deviating from the target load value.

22. The system of claim 21 in which:

said controller includes an annunciator responsive to an annunciator input to generate a sound output; and said processor is responsive to said load value output representing a force exceeding an upper effort limit having a limit value above said target load value to derive said annunciator input.

23. The system of claim 21 in which:

said processor is responsive to a load value output representing a force less than a lower effort threshold having a lower effort threshold load value below said target load value to derive a visual output signal providing an eighth prompt to the user to squeeze hand grip assembly harder.

24. A system for carrying out an isometric exercise regimen by a user, comprising:

a handgrip assembly including a load cell component responsive to compressive squeezing force applied by a hand of user to derive a load value output corresponding with the value of said force;

a display, responsive to a visual input signal to provide a visually perceptible display output;

first and second control members hand actuable to provide respective first and second control conditions;

a controller including a processor and a memory operationally associated therewith; and said processor, when enabled, being responsive to a second control condition to enter a stepped exercise configuration mode and derive a visual input signal providing a first prompt to the user to squeeze said handgrip assembly at maximum capability, responsive to said load value output to derive a visual input signal to provide a first cue displaying the maximum force value corresponding with said load value output, responsive to said first control condition to submit said maximum force value to memory, responsive to said first control condition to derive a visual input signal providing a second prompt to enter a desired number of a succession of steps of a trial, each said step corresponding with a memory retained assigned target load factor, hold interval and rest interval, responsive to said second control condition to elect a given number of said steps, responsive to said first control condition to derive a visual input signal providing a third prompt to enter a desired number of repetitions of said trial, responsive to said second control condition to elect a given number of repetitions, responsive in a stepped exercise mode to access memory retained assigned target load factor for a first said step and said maximum force value to compute a first step target load value, responsive to said first control condition to derive a visual input signal providing a fourth prompt to the user to commence a first step effort of said trial by applying squeezing force to said handgrip assembly at said first step target load value, responsive to access said memory retained hold and rest intervals assigned for said first step, responsive in the presence of a load value output to time-out said hold interval assigned for said first step, to derive a score value based upon the memory retained target load value and said load value output and to derive a comparison value representing the generally instantaneous relationship between said first step target load value and said value of force corresponding with said load value, responsive to derive a visual output signal providing a second cue to the user representing said comparison value, said score value and the status of said time-out of the hold interval assigned for said first step, responsive at the termination of the hold interval assigned for said first step to time-out said rest interval assigned for said first step and to derive a visual output signal providing a fifth prompt to the user of the presence of a rest interval, responsive at the termination of said rest interval assigned for said first step to reiterate said prompts and cues with respect to any next effort corresponding with any next step of the elected given number of steps in said sequence of steps of a trial, responsive at the completion of a trial to the elected given number of repetitions to reiterate said trial when the elected given number of repetitions is greater than one.

25. The system of claim 24 which:

said memory retained assigned target load factor is predetermined for each step of said elected given number of said steps of said succession of steps.

26. The system of claim 25 in which:

said memory retained assigned target load factor for each step in said succession of steps is unique for each step and is within a range from about 100% to about 20%.

27. The system of claim 24 in which:

said memory retained assigned hold interval is predetermined for each step of said elected given number of said steps of said succession of steps.

28. The system of claim 27 in which:

said memory retained assigned hold interval for each step on said succession of steps is unique for each step and is within a range from about 5 seconds to about 120 seconds.

29. The system of claim 24 in which:

said memory retained assigned rest interval for each step in said succession of steps is predetermined for each step of said elected given number of steps of said succession of steps.

30. The system of claim 29 in which:

said memory retained assigned rest interval for each step in said succession of steps is within a range from about 50 seconds to about 120 seconds.

31. The system of claim 24 in which:

said desired number of steps of said succession of steps may be elected from one step to about five steps.

32. The system of claim 24 in which:

a default number one, corresponding with said first step, is retained within said memory; and said processor is responsive, when in said stepped exercise configuration mode to enter one as said desired number of steps in the absence of said second control condition.

33. The system of claim 24 in which:

a default number four corresponding with said number of repetitions is retained within said memory; and said processor is responsive when in said stepped exercise configuration mode to enter four as said derived number of repetitions in the absence of said second control condition.

34. The system of claim 24 in which:

said controller includes a calendar circuit deriving a date output; and said processor is responsive to said date output to effect the recordation thereof in said memory in conjunction with said maximum force value and said score value.

35. The system of claim 34 in which:

said controller includes a data transfer port connectable with an interactive data communication system; and said processor is responsive to an input from said interactive data communications system to download said date output, said maximum force value and said score value.

36. The system of claim 24 in which:

said processor is responsive to said comparison value to derive a visual output signal providing the second cue as including a center pointer visual cue representing the target load value, and an effort dynamic bar graph visual cue having a top position present as a top aligned with said center pointer when said load value output represents a force equal to the target load value, the top line moving away from the center pointer when the load value output represents a force deviating from the target load value.

37. The system of claim 36 in which:

said controller includes an annunciator responsive to an annunciator input to generate a sound output; and said processor is responsive to said load value output representing a force exceeding an upper effort limit having a limit value above said target load value to derive said annunciator input.

38. The system of claim 36 in which:

said processor is responsive to a load value output representing a force less than a lower effort threshold having a lower effort threshold load value below said target load value to derive a visual output signal providing an eighth prompt to the user to squeeze said handgrip assembly harder.

39. The system of claim 24 in which:

said processor is responsive to a said load value output representing a predetermined percentage of said target load value for a given said step to effect commencement of the time-out of the hold interval corresponding with said given step.

40. A method for carrying our an isometric exercise by a user, comprising the steps of:

(a) providing a handgrip assembly including a load cell component responsive to compressive squeezing by a hand of the user to provide a load value output;

(b) providing a display having a visual readout;

(c) providing a memory;

(d) prompting the user at the display to apply a maximum effort squeezing said handgrip assembly;

(e) then monitoring any subsequent load value output;

(f) recording a maximum load value corresponding with the load value output monitored in step (e) in said memory;

(g) providing step data in memory said step data identifying a sequence of steps 1 through N, each said step having an assigned target load factor, an assigned hold interval, and an assigned rest interval;

(h) prompting the user at said display to elect a trial defining number of said steps of said sequence of 1 through N steps;

(i) recording the elected number of steps;

(j) determining a step 1 target load value with respect to said target load factor assigned for step 1 and said recorded maximum load value;

(k) prompting the user at said display to apply a squeezing force to said handgrip assembly at said step 1 target load value for the hold interval assigned to step 1;

(l) then monitoring subsequent load value outputs occurring during said hold interval assigned to step 1;

(m) cuing the user at said display during said hold interval of the comparative relationship between the load value outputs occurring during the hold interval and said step 1 target load value;

(n) deriving score values during said monitoring step (l), said score values corresponding with a comparison of said load value outputs with said step 1 target load value;

(o) prompting the user at said display to rest for the rest interval assigned to step 1; and (p) repeating said steps (j) through (o) in conjunction with the step number assigned target load factors, hold intervals and rest intervals commencing with step 2 of said sequence and ending with that step corresponding with the elected number of steps when the sequence number of steps recorded in step (i) exceeds one.

41. The method of claim 40 in which:

said step (h) further comprises the step; (h1) prompting said user at said display to elect a number of repetitions of said trial; and further comprising the step:

(q) repeating said trial established in steps (j) through (p) in accordance with said elected number of repetitions.

42. The method of claim 40 further comprising the step:

(r) recording in said memory a recording score value corresponding with said score values.

43. The method of claim 42 in which said recording score value of step (r) corresponds with a running average of said score values.

44. The method of claim 42 further comprising the step:

(s) recording the date of occurrence of said steps (f) and (r) in said memory.

45. The method of claim 44 in which: said step (c) further comprises the step:

(c1) providing an interactive communication port operably associated with said memory;

and further comprising the step:

(t) downloading the data recorded in memory in conjunction with steps (f), (r) and (s) from said interactive communications port to a data receiving facility.

46. The method of claim 40 in which said step (m) is carried out by providing as a visual cue, a center point representing target load value, and a target effort dynamic bar graph having a top position present as a top line aligned with said center point when a load value output corresponds in equality with said target load value, the top line moving away from the center point when said load value output deviates from said target load values.

47. The method of claim 40 in which:

said step (g) provides said step data wherein, for said sequence of steps 1 through N said assigned load factors are assigned from within a range from about 20% to about 100%.

48. The method of claim 40 in which:

said step (g) provides said step data wherein, for said sequence of steps 1 through N said assigned hold intervals are assigned from within a range from about 5 seconds to about 120 seconds.

49. The method of claim 40 in which:

said step (g) provides said step data wherein, for said sequence of steps 1 through N said assigned rest intervals are assigned from within a range from about 50 seconds to about 120 seconds.

50. The method of claim 43 including the step:
(u) prompting said user at said display of poor performance when said recording score value falls below a predetermined threshold value.

51. The method of claim 40 in which said step (e) further comprises the step:
(e1) prompting said user to squeeze again or proceed to step (f).

52. A method for carrying out an isometric exercise by a user, comprising the steps of:
(a) providing a handgrip assembly including a load cell component responsive to compressive squeezing by a hand of the user to provide load value output;
(b) providing a display having a visual readout;
(c) providing a memory;
(d) prompting the user at said display to apply a maximum effort squeezing said handgrip assembly;
(e) then monitoring any subsequent load value output;
(f) recording a maximum load value corresponding with a said load value output monitored in step (e) in said memory;
(g) providing electable target load factor values falling within a designated range of load factor values in memory;
(h) providing electable trial repetition numbers falling within a designated range of numbers in memory;
(i) providing electable hold intervals falling within a designated range of hold intervals in memory;
(j) providing electable rest intervals falling within a designated range of rest intervals in memory;
(k) prompting said user at said display to elect a said target load factor value from said designated range of load factor values provided in memory in conjunction with step (g);
(l) prompting the user at said display to elect a trial repetition number provided in memory in conjunction with step (h);
(m) prompting the user at said display to elect a the hold interval provided in memory in conjunction with step (i);
(n) prompting the user at said display to elect a rest interval provided in memory in conjunction with step (j);
(o) determining a target load value with respect to said target load factor value elected in conjunction with step (k) and said maximum load value recorded in conjunction with step (f);
(p) prompting the user at said display to apply a squeezing force to said handgrip assembly at said target load value determined in step (o) for the hold interval elected in conjunction with step (m);
(q) then monitoring subsequent load value outputs occurring during said elected hold interval;
(r) cueing the user at said display during said elected hold interval of the comparative relationship between said load value outputs occurring during said elected hold interval and said target load value determined in conjunction with step (o):
(s) deriving score values during said monitoring step (q), said score values corresponding with a comparison of load value outputs with said target load value;

(t) prompting the user at said display to rest for the rest interval elected in conjunction with step (n); and
(u) repeating steps (o) through (t) in correspondence with said trial repetition number elected in conjunction with step (l).

53. The method of claim 52 in which said step (g) provides electable target load factor values within a range of from about 10% to about 100%.

54. The method of claim 52 in which said step (h) provides said electable trial repetition numbers within a range of from about 5 seconds to about 120 seconds.

55. The method of claim 52 in which said step (i) provides said electable hold intervals within a range of from about 5 seconds to about 120 seconds.

56. The method of claim 52 in which said step (j) provides said electable rest intervals within a range of from about 10 seconds to about 180 seconds.

57. The method of claim 52 further comprising said step:
(v) recording in said memory provided in said step (c) a recording score value corresponding with said score values derived in said step (s).

58. The method of claim 57 in which said recording score value of step (v) corresponds with a running average of said score values.

59. The method of claim 58 further comprising the step:
(w) recording the date pf occurrence of said steps (t) and (v) in said memory.

60. The method of claim 59 in which:
said step (c) further comprises the step:
(c1) providing an interactive communication port operably associated with said memory;
and further comprising the step:
(x) downloading the data recorded in memory in conjunction with steps (f), (v) and (w) from said interactive communications port to a data receiving facility.

61. The method of claim 52 in which said step (r) is carried out by providing as a visual cue, a center point representing said target load value, and a target effort dynamic bar graph having a top position present as a top line aligned with the center point when a load value output corresponds in equality with said target load value, said top line moving away from the center point when the load value output deviates from the target load values.

62. The method of claim 52 in which:
said step (i) includes the step (i1) of providing a nominated hold interval corresponding with each electable target load factor value; and
said step (m) includes the step (m1) of selecting a nominated hold interval as the elected hold interval in the absence of a user election of a hold interval.

63. The method of claim 52 in which:
said step (j) includes the step (j1) of providing a nominated rest interval corresponding with each electable target load factor value; and
said step (n) includes the step (n1) of selecting a said nominated hold interval as said elected rest interval in the absence of a said user election of a said rest interval.

64. Apparatus for carrying out a protocol-based isometric exercise regimen, comprising:
a rigid housing having a hand grasping portion with first and second base grip components having respective outwardly disposed first and second elongate grasping surfaces, said first and second grip surfaces being spaced apart a first predetermined widthwise extent and said first base grip having a first base connector assembly adjacent the first grip surface thereof, said housing having an interacting portion fixed to and extending from the hand grasping portion;

an elongate rigid thrust plate positioned within the housing hand grasping portion in force transfer relationship with the first and second base grip components;

a load cell assembly coupled in stress transfer relationship with said thrust plate and having a force output signal in response to stress imposed from the first and second base grip components;

a control circuit within said housing responsive to said force output signal to provide an evaluation output;

a readout assembly mounted at said housing interaction portion, responsive to said evaluation output to provide a perceptible output corresponding therewith; and a first auxiliary grip component having a first auxiliary grasping surface and a first auxiliary connector assembly adjacent the first auxiliary grasping surface removably connectable with the first base connector assembly, when the first auxiliary connector assembly is connected with the first base connector assembly, the first auxiliary grasping surface being spaced from the second base grip second grasping surface a second predetermined widthwise extent greater than the first predetermined widthwise extent.

65. The apparatus of claim 64 in which:

said second base grip component includes a second base connector assembly adjacent the second elongate grasping surface thereof; and said first auxiliary grip component first auxiliary connector assembly is removably connectable with the second base connector assembly, when the first auxiliary connector assembly is connected with the second base connector assembly the first auxiliary grasping surface being spaced from said first base grip first grasping surface the second predetermined widthwise extent.

66. The apparatus of claim 64 in which:

said first auxiliary grip component is generally semi-cylindrical in shape, and said first auxiliary grasping surface is of an undulatory finger grasping configuration.

67. The apparatus of claim 64 in which:

said second base grip component includes a second base connector assembly adjacent the second elongate grasping surface thereof; and further comprising a second auxiliary grip component having a second auxiliary grasping surface and a second auxiliary connector assembly adjacent the second auxiliary grasping surface removably connectable with the first base connector assembly as said second base connector assembly, when the second auxiliary connector assembly is connected with the first or second base connector assembly said second auxiliary grasping surface being spaced from respective second or first grip surface the second predetermined widthwise extent.

68. The apparatus of claim 67 in which:

said second auxiliary grip component is generally semi-cylindrical in shape, and said second auxiliary grasping surface is generally of concave curvature effective to engage the palm of the hand.

69. The apparatus of claim 64 in which:

said second base grip component includes a second base connector assembly adjacent the second elongate grasping surface thereof; further comprising a second auxiliary grip component having a second auxiliary grasping surface and a second auxiliary connector assembly adjacent the second auxiliary grasping surface removably connectable with the first base connector assembly;

said first auxiliary grip component first auxiliary connector assembly is removably connectable with the second base connector assembly; and when said first auxiliary connector assembly is connected with said second base connector assembly and the second auxiliary connector assembly is connected with said first base connector assembly, the second auxiliary grasping surface is spaced from the first auxiliary grasping surface a third predetermined widthwise extent greater than the second predetermined widthwise extent.

70. The apparatus of claim 64 in which:

said readout assembly is mounted at said housing interaction portion in an angular orientation effective to be observed only from an eye station having a line of sight confronting said first base grip component.

71. A system for carrying out an isometric exercise regimen by a user, comprising:

a hand grip assembly including a load cell component responsive to compressive squeezing force applied by a hand of the user to derive a load value output corresponding with the value of said force;

a display, responsive to a visual input signal to provide a visually perceptible display output;

first and second control members hand actuable to provide respective first and second control conditions;

a controller including a processor and memory operatively associated therewith; and said processor being responsive to the first control condition to conditionally enter a diagnostic grip test mode providing a visual input signal deriving a first prompt at said display to actuate the first control member to enter the diagnostic grip test mode, is responsive to the second control condition to conditionally enter a therapy mode, and is then responsive to the first control condition to provide a visual input signal deriving a second prompt at said display to actuate the first control member to enter the therapy mode.

72. The system of claim 71 in which:

said processor is responsive in the presence of said first prompt to said first control condition to derive a visual input signal providing a third prompt to the user at said display to actuate the first control member to enter a maximum grip test therapy mode.

73. The system of claim 71 in which:

said processor is responsive in the presence of the first prompt to the second control condition to derive a visual input signal providing a fourth prompt at said display to actuate the first control member to enter a rapid exchange diagnostic mode.

74. The system of claim 71 in which:

said processor is responsive in the presence of the second prompt to the first control condition to derive a visual input signal providing a fifth prompt at said display to actuate the first control member to enter a fixed exercise therapy mode.

75. The system of claim 71 in which:

said processor is responsive in the presence of the second prompt to the second control condition to derive a visual input signal providing a sixth prompt at said display to actuate the first control member to enter a stepped exercise therapy mode.

76. A system for carrying out an isometric diagnostic regimen by a user, comprising:

a handgrip assembly including a load cell component responsive to compressive squeezing force applied by a hand of said user to derive a load value output corresponding with the value of said force;

a display, responsive to a visual input signal to provide a visually perceptible display output and to an audible input signal to provide an audibly perceptible cue output;

first and second control members hand actuateable to provide respective first and second control conditions;

a controller including a processor and memory operationally associated therewith; and said processor, when enabled, being responsive to said second control condition to enter a rapid exchange test mode to carry out an alternating user hand sequence of N maximum squeezing force trials at a timed repetition rate of period $t_r$, responsive to said first control condition to derive said visual input signal providing a starting trial prompt, is responsive to an initial load value output generated with one hand of said user to derive a visual input signal providing a force value cue and is responsive to time an initial said period $t_r$ and to derive an audible input signal at the timeout of said period, $t_r$, and submit said value of said force corresponding with said initial load value output to said memory, and responsive to reiterate said derivation of said visual input signal, timing of said period, $t_r$, in response to timeout of the next previous period $t_r$, and the derivation of a corresponding said visual input signal providing a force value cue, generating said audible input signal at the timeout of said period $t_r$, and submittal of a corresponding said value of said force corresponding with said load value to said memory for a total of N trials, and responsive at the termination of the Nth said trial to compute the average value of force, standard deviation and coefficient of variation for said N trials, responsive to derive a visual input signal corresponding with said computed average value of force, standard deviation of memory retained force values and the corresponding coefficient of variation for said N trials; and said processor, when enabled, is responsive to said second control condition to enter a configuration mode wherein said visual input signals are electable by subsequent actuation of said first and second control members.

77. The system of claim 76 in which:

said processor is enabled by initial response to said first control condition.

78. A system for carrying out an isometric diagnostic regimen by a user, comprising:

a handgrip assembly including a load cell component responsive to compressive squeezing force applied by a hand of said user to derive a load value output corresponding with the value of said force;

a display, responsive to a visual input signal to provide a visually perceptible display output and to an audible input signal to provide an audibly perceptible cue output;

first and second control members hand actuateable to provide respective first and second control conditions;

a controller including a processor and memory operationally associated therewith;

said processor, when enabled, being responsive to said second control condition to enter a rapid exchange test mode to carry out an alternating user hand sequence of N maximum squeezing force trials at a timed repetition rate of period $t_r$, responsive to said first control condition to derive a visual input signal providing a starting trial prompt, is responsive to an initial load value output generated with one hand of said user to derive a visual input signal providing a force value cue and is responsive to time an initial said period $t_r$ and to derive an audible input signal at the timeout of said period, $t_r$, and submit said value of said force corresponding with said initial load value output to said memory, and responsive to reiterate said derivation of said visual input signal, timing of said period, $t_r$, in response to timeout of the next previous period $t_r$, and the derivation of a corresponding said visual input signal providing a force value cue, generating said audible input signal at the timeout of said period $t_r$, and submittal of a corresponding said value of said force corresponding with said load value to said memory for a total of N trials, and responsive at the termination of the Nth said trial to compute the average value of force, standard deviation and coefficient of variation for said N trials, responsive to derive a visual input signal corresponding with said computed average value of force, standard deviation of memory retained force values and the corresponding coefficient of variation for said N trials; and said processor, when enabled, is responsive to said second control condition to enter a configuration mode wherein the number, N, of maximum squeezing force trials to be carried out when in said rapid exchange test mode is electable by subsequent actuation of said first and second control members.

79. The system of claim 78 in which:

said processor is enabled by initial response to said first control condition.

80. A system for carrying out an isometric diagnostic regimen by a user, comprising:

a handgrip assembly including a load cell component responsive to compressive squeezing force applied by a hand of said user to derive a load value output corresponding with the value of said force;

a display, responsive to a visual input signal to provide a visually perceptible display output and to an audible input signal to provide an audibly perceptible cue output;

first and second control members hand actuateable to provide respective first and second control conditions;

a controller including a processor and memory operationally associated therewith;

said processor, when enabled, being responsive to said second control condition to enter a rapid exchange test mode to carry out an alternating user hand sequence of N maximum squeezing force trials at a timed repetition rate of period $t_r$, responsive to said first control condition to derive a visual input signal providing a starting trial prompt, is responsive to an initial load value output generated with one hand of said user to derive a visual input signal providing a force value cue and is responsive to time an initial said period $t_r$ and to derive an audible input signal at the timeout of said period, $t_r$, and submit said value of said force corresponding with said initial load value output to said memory, and responsive to reiterate said derivation of said visual input signal, timing of said period, $t_r$, in response to timeout of the next previous period $t_r$, and the derivation of a corresponding said visual input signal providing a force value cue, generating said audible input signal at the timeout of said period $t_r$, and submittal of a corresponding said value of said force corresponding with said load value to said memory for a total of N trials, and responsive at the termination of the Nth said trial to compute the average value of force, standard deviation and coefficient of variation for said N trials, responsive to derive a visual input signal corresponding with said computed average value of force, standard deviation of memory retained force values and the corresponding coefficient of variation for said N trials; and said processor, when enabled, is responsive to said second control condition to enter a configuration mode wherein said repetition rate period $t_r$, of maximum squeezing force trials to be carried out when in said rapid exchange test mode is electable by subsequent actuation of said first and second control members.

81. The system of claim 80 in which:

said processor is enabled by initial response to said first control condition.

82. A system for carrying out an isometric exercise regimen by a user, comprising:

a handgrip assembly including a load cell component responsive to compressive squeezing force applied by a hand of said user to derive a load value output corresponding with the value of said force;

a display, responsive to a visual input signal to provide a visually perceptible display output;

first and second control members hand actuateable to provide respective first and second control conditions;

a controller including a processor and memory operationally associated therewith;

said processor, when enabled, being responsive to said second control condition to enter a fixed exercise configuration mode and derive a visual input signal providing a first prompt to said user to squeeze said handgrip assembly at maximum capability, responsive to said load value output to derive a visual input signal providing a first cue displaying the maximum force value corresponding with said load value output, responsive to said first control condition to submit said maximum force value to said memory, responsive to said first control condition to derive a visual input signal providing a second prompt to enter a desired target load factor, responsive to said second control condition to derive a desired target load factor, responsive to said desired target load factor and said memory retained maximum force value to compute a target load value and submit said target load value to said memory, responsive to said first control condition to derive a said visual input signal providing a third prompt to enter a desired trial repetition number, responsive to a second control condition to derive a desired trial repetition number for submittal to said memory, responsive to said first control condition to derive a said visual input signal providing a fourth prompt to enter a desired target load hold interval, responsive to a second control condition to derive a desired target load hold interval for submittal to said memory, responsive to said first control condition to derive a visual input signal providing a fifth prompt to enter a desired inter-trial rest interval, responsive to a second control condition to derive a desired inter-trial rest interval for submittal to said memory, responsive to said first control condition to derive a visual input signal providing a sixth prompt to said user to commence a trial by applying squeezing force to said handgrip assembly at said target load value, responsive in the presence of a load value output to time-out said memory retained desired target load hold interval, to derive a score value based upon said memory retained target load value and said load value output and to derive a comparison value representing the generally instantaneous relationship between said target load value and said value of force corresponding with said load value output, responsive to derive a visual output signal providing a second cue to said user representing said comparison value, said score value and the status of said time-out of said hold interval, responsive at the termination of said target load hold interval to time-out said desired inter-trial rest interval and to derive a visual input signal providing a seventh prompt to said user of the presence of said inter-trial rest interval, and responsive at the termination of said inter-trial rest interval, to said desired trial repetition number to reiterate said commencement of a trial by deriving said sixth prompt;

said processor is responsive when in said fixed exercise configuration mode to said second control condition to enter a derived target load factor from within a permissible load range from about 10% to about 100%;

said processor is responsive when in said fixed exercise mode to nominate a memory retained predetermined value for said target load hold interval;

is responsive when in said fixed exercise mode to enter said predetermined value for said target load hold interval as said desired target load hold interval in the absence of said second control condition; and said predetermined value for said target load value interval is nominated from within a range from about 5 seconds to about 120 seconds.

83. A system for carrying out an isometric exercise regimen by a user, comprising:

a handgrip assembly including a load cell component responsive to compressive squeezing force applied by a hand of said user to derive a load value output corresponding with the value of said force;

a display, responsive to a visual input signal to provide a visually perceptible display output;

first and second control members hand actuateable to provide respective first and second control conditions;

a controller including a processor and memory operationally associated therewith;

said processor, when enabled, being responsive to a second control condition to enter a fixed exercise configuration mode and derive a visual input signal providing a first prompt to said user to squeeze said handgrip assembly at maximum capability, responsive to said load value output to derive a visual input signal providing a first cue displaying the maximum force value corresponding with said load value output, responsive to said first control condition to submit said maximum force value to said memory, responsive to said first control condition to derive a visual input signal providing a second prompt to enter a desired target load factor, responsive to said second control condition to derive a desired target load factor, responsive to said desired target load factor and said memory retained maximum force value to compute a target load value and submit said target load value to said memory, responsive to said first control condition to derive a visual input signal providing a third prompt to enter a desired trial repetition number, responsive to a second control condition to derive a desired trial repetition number for submittal to said memory, responsive to said first control condition to derive a visual input signal providing a fourth prompt to enter a desired target load hold interval, responsive to a second control condition to derive a desired target load hold interval for submittal to said memory, responsive to said first control condition to derive a visual input signal providing a fifth prompt to enter a desired inter-trial rest interval, responsive to a second control condition to derive a desired inter-trial rest interval for submittal to said memory, responsive to said first condition to derive a visual input signal providing a sixth prompt to said user to commence a trial by applying squeezing force to said handgrip assembly at said target load value, responsive in the presence of a load value output to time-out said memory retained desired target load hold interval, to derive a score value based upon said memory retained target load value and said load value output and to derive a comparison value representing the generally instantaneous relationship between said target load value and said value of force corresponding with said load value output, responsive to derive a visual output signal providing a second cue to said user representing said comparison value, said score value and the status of said time-out of said hold interval, responsive at the termination of said target load hold interval to time-out said desired inter-trial rest interval and to derive a visual input signal providing a seventh prompt to said user of the presence of said inter-trial rest interval, and responsive at the termination of said inter-trial rest interval, to said desired trial repetition number to reiterate said commencement of a trial by deriving said sixth prompt;

said processor is responsive when in said fixed exercise configuration mode to said second control condition to enter a derived target load factor from within a permissible load range from about 10% to about 100%;

said processor is responsive when in said fixed exercise mode to nominate a memory retained predetermined value for said inter-trial rest interval;

is responsive when in said fixed exercise mode to enter said predetermined value for said inter-trial rest interval as said desired inter-trial test interval in the absence of said second control condition; and said predetermined value for said inter-trial rest interval is nominated from within a range from about 50 seconds to about 120 seconds.

84. A system for carrying out an isometric exercise regimen by a user, comprising:

a handgrip assembly including a load cell component responsive to compressive squeezing force applied by a hand of said user to derive a load value output corresponding with the value of said force;

a display, responsive to a visual input signal to provide a visually perceptible display output;

first and second control members hand actuateable to provide respective first and second control conditions;

a controller including a processor and memory operationally associated therewith; and said processor, when enabled, being responsive to a second control condition to enter a fixed exercise configuration mode and derive a visual input signal providing a first prompt to said user to squeeze said handgrip assembly at maximum capability, responsive to said load value output to derive a visual input signal providing a first cue displaying the maximum force value corresponding with said load value output, responsive to said first control condition to submit said maximum force value to said memory, responsive to said first control condition to derive a visual input signal providing a second prompt to enter a desired target load factor, responsive to said second control condition to derive a desired target load factor, responsive to said desired target load factor and said memory retained maximum force value to compute a target load value and submit said target load value to said memory, responsive to said first control condition to derive a visual input signal providing a third prompt to enter a desired trial repetition number, responsive to a second control condition to derive a desired trial repetition number for submittal to said memory, responsive to said first control condition to derive a visual input signal providing a fourth prompt to enter a desired target load hold interval, responsive to a second control condition to derive a desired target load hold interval for submittal to said memory, responsive to said first control condition to derive a visual input signal providing a fifth prompt to enter a desired inter-trial rest interval, responsive to a second control condition to derive a desired inter-trial rest interval for submittal to said memory, responsive to said first condition to derive a visual input signal providing a sixth prompt to said user to commence a trial by applying squeezing force to said handgrip assembly at said target load value, responsive in the presence of a load value output to time-out said memory retained desired target load hold interval, to derive a score value based upon said memory retained target load value and said load value output and to derive a comparison value representing the generally instantaneous relationship between said target load value and said value of force corresponding with said load value output, responsive to derive a visual output signal providing a second cue to said user representing said comparison value, said score value and the status of said time-out of said hold interval, responsive at the termination of said target load hold interval to time-out said desired inter-trial rest interval and to derive a visual input signal providing a seventh prompt to said user of the presence of said inter-trial rest interval, and responsive at the termination of said inter-trial rest interval, to said desired trial repetition number to reiterate said commencement of a trial by deriving said sixth prompt; and said processor is responsive when in said fixed exercise configuration mode to said second control condition to enter a desired target load hold interval value from within a permissible value range from about 5 seconds to about 120 seconds.

85. A system for carrying out an isometric exercise regimen by a user, comprising:

a handgrip assembly including a load cell component responsive to compressive squeezing force applied by a hand of said user to derive a load value output corresponding with the value of said force;

a display, responsive to a visual input signal to provide a visually perceptible display output;

first and second control members hand actuateable to provide respective first and second control conditions;

a controller including a processor and memory operationally associated therewith;

said processor, when enabled, being responsive to a second control condition to enter a fixed exercise configuration mode and derive a visual input signal providing a first prompt to said user to squeeze said handgrip assembly at maximum capability, responsive to said load value output to derive a visual input signal providing a first cue displaying the maximum force value corresponding with said load value output, responsive to said first control condition to submit said maximum force value to said memory, responsive to said first control condition to derive a visual input signal providing a second prompt to enter a desired target load factor, responsive to said second control condition to derive a desired target load factor, responsive to said desired target load factor and said memory retained maximum force value to compute a target load value and submit said target load value to said memory, responsive to said first control condition to derive a visual input signal providing a third prompt to enter a desired trial repetition number, responsive to a second control condition to derive a desired trial repetition number for submittal to said memory, responsive to said first control condition to derive a visual input signal providing a fourth prompt to enter a desired target load hold interval, responsive to a second control condition to derive a desired target load hold interval for submittal to said memory, responsive to said first control condition to derive a visual input signal providing a fifth prompt to enter a desired inter-trial rest interval, responsive to a second control condition to derive a desired inter-trial rest interval for submittal to said memory, responsive to said first control condition to derive a visual input signal providing a sixth prompt to said user to commence a trial by applying squeezing force to said handgrip assembly at said target load value, responsive in the presence of a load value output to time-out said memory retained desired target load hold interval, to derive a score value based upon said memory retained target load value and said load value output and to derive a comparison value representing the generally instantaneous relationship between said target load value and said value of force corresponding with said load value output, responsive to derive a visual output signal providing a second cue to said user representing said comparison value, said score value and the status of said time-out of said hold interval, responsive at the termination of said target load hold interval to time-out said desired inter-trial rest interval and to derive a visual input signal providing a seventh prompt to said user of the presence of said inter-trial rest interval, and responsive at the termination of said inter-trial rest interval, to said desired trial repetition number to reiterate said commencement of a trial by deriving said sixth prompt; and said processor is responsive when in said fixed exercise configuration mode to said second control condition to enter a desired inter-trial rest interval value from a permissible value range from about 5 seconds to about 120 seconds.

86. A system for carrying out an isometric exercise regimen by a user, comprising:

a handgrip assembly including a load cell component responsive to compressive squeezing force applied by a hand of said user to derive a load value output corresponding with the value of said force;

a display, responsive to a visual input signal to provide a visually perceptible display output;

first and second control members hand actuateable to provide respective first and second control conditions;

a controller including a processor and memory operationally associated therewith;

said processor, when enabled, being responsive to a second control condition to enter a fixed exercise configuration mode and derive a visual input signal providing a first prompt to said user to squeeze said handgrip assembly at maximum capability, responsive to said load value output to derive a visual input signal providing a first cue displaying the maximum force value corresponding with said load value output, responsive to said first control condition to submit said maximum force value to said memory, responsive to said first control condition to derive a visual input signal providing a second prompt to enter a desired target load factor, responsive to said second control condition to derive a desired target load factor, responsive to said desired target load factor and said memory retained maximum force value to compute a target load value and submit said target load value to said memory, responsive to said first control condition to derive a visual input signal providing a third prompt to enter a desired trial repetition number, responsive to a second control condition to derive a desired trial repetition number for submittal to said memory, responsive to said first control condition to derive a visual input signal providing a fourth prompt to enter a desired target load hold interval, responsive to a second control condition to derive a desired target load hold interval for submittal to said memory, responsive to said first control condition to derive a visual input signal providing a fifth prompt to enter a desired inter-trial rest interval, responsive to a second control condition to derive a desired inter-trial rest interval for submittal to said memory, responsive to said first condition to derive a visual input signal providing a sixth prompt to said user to commence a trial by applying squeezing force to said handgrip assembly at said target load value, responsive in the presence of a load value output to time-out said memory retained desired target load hold interval, to derive a score value based upon said memory retained target load value and said load value output and to derive a comparison value representing the generally instantaneous relationship between said target load value and said value of force corresponding with said load value output, responsive to derive a visual output signal providing a second cue to said user representing said comparison value, said score value and the status of said time-out of said hold interval, responsive at the termination of said target load hold interval to time-out said desired inter-trial rest interval and to derive a visual input signal providing a seventh prompt to said user of the presence of said inter-trial rest interval, and responsive at the termination of said inter-trial rest interval, to said desired trial repetition number to reiterate said commencement of a trial by deriving said sixth prompt;

a default target hold interval of about 120 seconds is retained within said memory; and said processor is responsive when in said fixed exercise configuration mode to enter said default target hold interval as said desired target hold interval in the absence of said second control condition.

87. A system for carrying out an isometric exercise regimen by a user, comprising:

a handgrip assembly including a load cell component responsive to compressive squeezing force applied by a hand of said user to derive a load value output corresponding with the value of said force;

a display, responsive to a visual input signal to provide a visually perceptible display output;

first and second control members hand actuateable to provide respective first and second control conditions;

a controller including a processor and memory operationally associated therewith;

said processor, when enabled, being responsive to a second control condition to enter a fixed exercise configuration mode and derive a visual input signal providing a first prompt to said user to squeeze said handgrip assembly at maximum capability, responsive to said load value output to derive a visual input signal providing a first cue displaying the maximum force value corresponding with said load value output, responsive to said first control condition to submit said maximum force value to said memory, responsive to said first control condition to derive a visual input signal providing a second prompt to enter a desired target load factor, responsive to said second control condition to derive a desired target load factor, responsive to said desired target load factor and said memory retained maximum force value to compute a target load value and submit said target load value to said memory, responsive to said first control condition to derive a visual input signal providing a third prompt to enter a desired trial repetition number, responsive to a second control condition to derive a desired trial repetition number for submittal to said memory, responsive to said first control condition to derive a visual input signal providing a fourth prompt to enter a desired target load hold interval, responsive to a second control condition to derive a desired target load hold interval for submittal to said memory, responsive to said first control condition to derive a visual input signal providing a fifth prompt to enter a desired inter-trial rest interval, responsive to a second control condition to derive a desired inter-trial rest interval for submittal to said memory, responsive to said first condition to derive a visual input signal providing a sixth prompt to said user to commence a trial by applying squeezing force to said handgrip assembly at said target load value, responsive in the presence of a load value output to time-out said memory retained desired target load hold interval, to derive a score value based upon said memory retained target load value and said load value output and to derive a comparison value representing the generally instantaneous relationship between said target load value and said value of force corresponding with said load value output, responsive to derive a visual output signal providing a second cue to said user representing said comparison value, said score value and the status of said time-out of said hold interval, responsive at the termination of said target load hold interval to time-out said desired inter-trial rest interval and to derive a visual input signal providing a seventh prompt to said user of the presence of said inter-trial rest interval, and responsive at the termination of said inter-trial rest interval, to said desired trial repetition number to reiterate said commencement of a trial by deriving said sixth prompt;

a default inter-trial rest interval of about 60 seconds is retained within said memory; and said processor is responsive when in said fixed exercise configuration mode to enter said default inter-trial rest interval as said desired inter-trial rest interval in the absence of said second control condition.

88. A system for carrying out an isometric exercise regimen by a user, comprising:

a handgrip assembly including a load cell component responsive to compressive squeezing force applied by a hand of said user to derive a load value output corresponding with the value of said force;

a display, responsive to a visual input signal to provide a visually perceptible display output;

first and second control members hand actuateable to provide respective first and second control conditions;

a controller including a processor and memory operationally associated therewith;

said processor, when enabled, being responsive to a second control condition to enter a fixed exercise configuration mode and derive a visual input signal providing a first prompt to said user to squeeze said handgrip assembly at maximum capability, responsive to said load value output to derive a visual input signal providing a first cue displaying the maximum force value corresponding with said load value output, responsive to said first control condition to submit said maximum force value to said memory, responsive to said first control condition to derive a visual input signal providing a second prompt to enter a desired target load factor, responsive to said second control condition to derive a desired target load factor, responsive to said desired target load factor and said memory retained maximum force value to compute a target load value and submit said target load value to said memory, responsive to said first control condition to derive a visual input signal providing a third prompt to enter a desired trial repetition number, responsive to a second control condition to derive a desired trial repetition number for submittal to said memory, responsive to said first control condition to derive a visual input signal providing a fourth prompt to enter a desired target load hold interval, responsive to a second control condition to derive a desired target load hold interval for submittal to said memory, responsive to said first control condition to derive a visual input signal providing a fifth prompt to enter a desired inter-trial rest interval, responsive to a second control condition to derive a desired inter-trial rest interval for submittal to said memory, responsive to said first condition to derive a visual input signal providing a sixth prompt to said user to commence a trial by applying squeezing force to said handgrip assembly at said target load value, responsive in the presence of a load value output to time-out said memory retained desired target load hold interval, to derive a score value based upon said memory retained target load value and said load value output and to derive a comparison value representing the generally instantaneous relationship between said target load value and said value of force corresponding with said load value output, responsive to derive a visual output signal providing a second cue to said user representing said comparison value, said score value and the status of said time-out of said hold interval, responsive at the termination of said target load hold interval to time-out said desired inter-trial rest interval and to derive a visual input signal providing a seventh prompt to said user of the presence of said inter-trial rest interval, and responsive at the termination of said inter-trial rest interval, to said desired trial repetition number to reiterate said commencement of a trial by deriving said sixth prompt;

said processor is responsive to a said load value output representing a predetermined percentage of said computed target load value to effect commencement of said time-out of said desired target load hold interval; and said predetermined percentage is about 10%.

89. A method for carrying out an isometric exercise by a user, comprising the steps of:

(a) providing an isometric exercising mechanism responsive to a force applied from an elected exercisable muscle group of the musculature of the user to provide a load value output;

(b) providing a memory;

(c) providing a display having a visibly perceptible readout;

(d) providing in said memory a mandated minimum number of one or more exercise steps;

(e) providing in said memory a mandated range of factors corresponding with one or more level of effort force steps to be carried out with said elected muscle group representing a beneficial exercise regimen;

(f) providing a mandated range of maximum values for hold intervals for each said level of effort force step representing a beneficial exercise regimen for said elected muscle group;

(g) providing in said memory one or more mandated minimum rest interval values between successive said level of effort force steps representing a beneficial exercise regimen for said elected muscle group;

(h) providing in said memory a test maximum effort interval beneficial for testing a maximum strength of said elected muscle group;

(i) prompting the user at said display to apply a force to said exercising mechanism at a maximum effort with the elected region of the musculature for said test maximum effort interval;

(j) then monitoring any subsequent load value output;

(k) recording a maximum load value corresponding with a load value monitored in step (c) in said memory;

(l) electing a number of exercise steps equal to or less than said mandated maximum number of exercising steps provided in step (d);

(m) deriving a target effort level load value for each said step elected in step (l) by applying a corresponding mandated factor provided in step (e) to said maximum load value recorded in step (k);

(n) prompting said user at said display to apply said force to said exercising mechanism with said elected region of the musculature at said target effort level load value derived in step (m) for the corresponding hold interval provided in step (f);

(o) monitoring said load value output during said hold interval of said step (n);

(p) cueing said user at said display during said hold interval of the comparative relationship between said load value outputs occurring during said hold interval of step (n) and said target effort level load value derived in conjunction with step (m); and (q) reiterating steps (n) through (p) for the number of exercise steps provided with step (d).

90. The method of claim 89 further comprising the step of:

(r) prompting said user at said display of the time of the rest interval provided in step (q) corresponding with each successive said step elected in step (l).

91. The method of claim 89 in which step (k) further comprises the step:

(k1) providing in said memory an elected range of factors corresponding with one or more level of effort force steps having values equal to or less than the values of said mandated range of factors provided in step (e).

92. The method of claim 89 in which said step (k) further comprises the step:

(k2) providing in said memory an elected range of values for hold intervals having values for hold intervals for each said level of effort force step equal to or less than said mandated range of maximum values for hold intervals provided in step (f).

93. The method of claim 89 in which said step (k) further comprises the step:

(k3) providing in said memory one or more elected rest intervals between successive said level of effort force steps having interval values equal to or more than said mandated minimum rest interval values provided in step (g).

94. The method of claim 89 in which:

said exercisable region of the musculature of said user is elected from the group comprising:

jaw muscles, neck muscles, shoulder muscles, upper arm muscles, lower arm muscles, hand muscles, finger muscles, diaphragm muscles, abdominal muscles, lower back muscles, upper leg muscles, lower leg muscles, ankle muscles, foot muscles, and toe muscles.

95. The method of claim 89 further comprising the step:

(s) providing compliance scores at said display during said exercise.

96. The method of claim 89 further comprising the step of:

(t) establishing a goal strength by measuring the maximum strength of an unimpaired muscle group contralateral to said elected muscle group.

97. A method for carrying out an isometric exercise by a user, comprising the steps of:

(a) providing a handgrip assembly including a load cell component responsive to compressive squeezing by a hand of the user to provide load value output;

(b) providing a display having a visual readout;

(c) providing a memory;

(d) prompting the user at said display to apply a maximum effort squeezing said handgrip assembly;

(e) then monitoring any subsequent load value output;

(f) recording a maximum load value corresponding with said load value output monitored in step (e) in said memory;

(g) providing electable target load factor values falling within a designated range of load factor values in memory;

(h) providing electable trial repetition numbers falling within a designated range of numbers in memory;

(i) providing electable hold intervals falling within a designated range of hold intervals in memory;

(j) providing electable rest intervals falling within a designated range of rest intervals in memory;

(k) prompting the user at said display to elect a target load factor value from said designated range of load factor values provided in memory in conjunction with step (g);

(l) prompting the user at said display to elect a trial repetition number provided in memory in conjunction with step (h);

(m) prompting the user at said display to elect a hold interval provided in memory in conjunction with step (i);

(n) prompting the user at said display to elect a rest interval provided in memory in conjunction with step (j);

(o) determining a target load value with respect to said target load factor value elected in conjunction with step (k) and said maximum load value recorded in conjunction with step (f);

(p) prompting the user at said display to apply a squeezing force to said handgrip assembly at said target load value determined in step (o) for the hold interval elected in conjunction with step (m);

(q) then monitoring subsequent load value outputs occurring during said elected hold interval;

(r) cueing the user at said display during said elected hold interval of the comparative relationship between said load value outputs occurring during said elected hold interval and said target load value determined in conjunction with step (o);

(s) deriving score values during said monitoring step (q), said score values corresponding with a comparison of load value outputs with said target load value;

(t) prompting the user at said display to rest for the rest interval elected in conjunction with step (n); and (u) repeating steps (o) through (t) in correspondence with said trial repetition number elected in conjunction with step (l).

98. The method of claim 97 in which said step (g) provides electable target load factor values within a range of from about 10% to about 100%.

99. The method of claim 97 in which said step (h) provides said electable trial repetition numbers within a range of from about 5 seconds to about 120 seconds.

100. The method of claim 97 in which said step (i) provides said electable hold intervals within a range of from about 5 seconds to about 120 seconds.

101. The method of claim 97 in which said step (j) provides said electable rest intervals within a range of from about 10 seconds to about 180 seconds.

102. The method of claim 97 further comprising said step:

(v) recording in said memory provided in said step (c) a recording score value corresponding with said score values derived in said step (s).

103. The method of claim 102 in which said recording score value of step (v) corresponds with a running average of said score values.

104. The method of claim 103 further comprising the step:

(w) recording the date pf occurrence of said steps (t) and (v) in said memory.

105. The method of claim 104 in which:

said step (c) further comprises the step:

(c1) providing an interactive communication port operably associated with said memory;

and further comprising the step:

(x) downloading the data recorded in memory h conjunction with steps (f), (v) and (w) from said interactive communications port to a data receiving facility.

106. The method of claim 97 which said step (r) is carried out by providing as a visual cue, a center point representing said target load value, and a target effort dynamic bar graph having a top position present as a top line aligned with the center point when a load value output corresponds in equality with said target load value, said top line moving away from the center point when the load value output deviates from the target load values.

107. The method of claim 97 in which:

said step (i) includes the step (i1) of providing a nominated hold interval corresponding with each electable target load factor value; and said step (m) includes the step (m1) of selecting a nominated hold interval as the elected hold interval in the absence of a user election of a hold interval.

108. The method of claim 97 which:

said step (j) includes the step (j1) of providing a nominated rest interval corresponding with each electable target load factor value; and said step (n) includes the step (n1) of selecting a said nominated hold interval as said elected rest interval in the absence of a said user election of a said rest interval.

* * * * *